United States Patent
Harris

(10) Patent No.: US 6,309,687 B1
(45) Date of Patent: *Oct. 30, 2001

(54) ANTI-FIRST-PASS EFFECT COMPOUNDS

(76) Inventor: James W. Harris, 180 Pinellas La. #101, Cocoa Beach, FL (US) 32933

(*) Notice: Subject to any disclaimer, the term of this patent is extended or adjusted under 35 U.S.C. 154(b) by 0 days.

This patent is subject to a terminal disclaimer.

(21) Appl. No.: 09/644,860

(22) Filed: Aug. 24, 2000

Related U.S. Application Data

(63) Continuation of application No. 09/455,911, filed on Dec. 7, 1999, which is a continuation of application No. 09/255,874, filed on Feb. 23, 1999, now Pat. No. 6,054,477, which is a continuation of application No. 08/977,259, filed on Dec. 23, 1997, now Pat. No. 6,063,809

(60) Provisional application No. 60/056,382, filed on Aug. 26, 1997.

(51) Int. Cl.[7] .............................. A23C 2/00; A23C 3/36; A23C 1/212; A61K 31/35

(52) U.S. Cl. ................. 426/330.5; 426/333; 426/616; 514/453; 514/454; 549/264; 549/334

(58) Field of Search ..................... 514/453, 454; 549/264, 334; 426/330.5, 333, 616

(56) References Cited

U.S. PATENT DOCUMENTS

| | | | | |
|---|---|---|---|---|
| 5,061,502 | * | 10/1991 | Cully et al. | 426/105 |
| 5,362,714 | * | 11/1994 | Radford et al. | 512/5 |
| 6,054,477 | * | 4/2000 | Harris | 514/453 |
| 6,063,809 | * | 5/2000 | Harris | 514/453 |

\* cited by examiner

*Primary Examiner*—Alan L. Rotman
*Assistant Examiner*—Raymond Covington

(57) ABSTRACT

Safe, effective first-pass inhibiting compounds and citrus-derived substances are provided. Formulations containing the compounds are also provided as are methods for inhibiting the first pass effect.

20 Claims, 2 Drawing Sheets

ANTI-FIRST-PASS EFFECT COMPOUNDS

This application is a Continuation of application Ser. No. 09/455,911, filed on Dec. 7, 1999, now U.S. Pat. No. 6,162,479; which is a Continuation of Ser. No. 09/255,874, filed Feb. 23, 1999, now U.S. Pat. No. 6,054,477; which is a Continuation of Ser. No. 08/997,259, filed Dec. 23, 1997, now U.S. Pat. No. 6,063,809. This application claims priority of Provisional Application Ser. No. 60/056,382, filed Aug. 26, 1997.

BACKGROUND OF THE INVENTION

1. Field of the Invention

The present invention relates to anti-first-pass effect compounds, compositions, and methods for their use, preparation, synthesis, and formulation. Preferably, the invention compounds and compositions are provided as a dietary supplement or as a medical food or as some other type of food product, or as a drug, pharmaceutical or drug preparation, or in some other physical form. In addition to any other function they have, the invention compounds and compositions function as inhibitors of the first-pass effect of orally-administered drugs. Beneficiaries of this invention are animals, preferably mammals, particularly humans, who require drugs, etc. subject to the first-pass effect.

2. Discussion of the Background

The "first-pass effect" of drugs given orally refers to the process of drug degradation during a drug's transition from initial ingestion to circulation in the blood stream. Often discussed in terms of "bioavailability", it is not uncommon for a drug that is administered to a patient orally to be given in a 5-fold or greater amount than ultimately necessary due to the degradation that occurs in the patient's body after intake. For example, the impact of the first-pass effect can be demonstrated with the case of the antihistamine terfenadine, wherein 99.5% of a tablet given by mouth is quickly changed to metabolites; hence, the bioavailability of terfenadine is approximately 0.5% (D. Garteiz et al., Arzneim.-Forsch., 1982; 32:1185–1190). As a further example, cyclosporin A, administered to organ transplant patients, has a median oral bioavailability of approximately 30% and a bioavailability range of approximately 8–92% among patients. Because of this large interindividual variation in cyclosporin bioavailability, frequent monitoring of blood concentrations during therapy initiation is necessary.

The inhibition of a particular xenobiotic metabolism as a mechanism of action generally, as well as the inhibition of the first-pass effect with chemical agents specifically, is well known in the art and has been for some time. Examples include the treatment of methanol (wood alcohol) poisoning with ethanol and the inhibition of the first-pass effect of cyclosporin with ketoconazole. See, for example, First, R. M. et al., The Lancet, 1198, Nov. 18, 1989, incorporated herein by reference.

Although the agent(s), enzyme type(s), biological processes, etc. responsible for the first-pass effect have not been fully identified, research has focused on agents capable of inhibiting the cytochrome P450 system. Inhibition of the P450 system is a model for in vitro determination of in vivo bioavailability enhancement. See, e.g., U.S. Pat. Nos. 5,478,723 and 5,567,592, both incorporated herein by reference, for a more full description of the P450 system. As reported by A. Keogh et al. (N. Eng. J. Med., Vol. 333, No. 10, p. 628, 1995) and S. Butman et al. (J. Heart Lung Transpl., Vol. 10, No. 3, p. 351, 1991), the dose of cyclosporin required by heart transplant patients could be reduced by approximately 85% when cyclosporin was co-administered with ketoconazole. In economic terms, both references estimated the cost savings to be equal to approximately $5,000 per year per patient. Other drugs which are subject to the first-pass effect and whose bioavailability is increased by inhibitors commonly given to humans include midazolam (K. Olkkola et al, Clin. Pharmacol. Ther., 1993, 53:298–305), terfenadine (Seldane®) (P. Honig et al., JAMA, Vol. 269, No. 12, 1513, 1993) and triazolam (Varhe, A. et al, Clin. Pharmocol. Ther., 1994, 56:601–7).

In addition to ketoconazole, the drugs fluconazole, ritonavir, itraconazole, miconazole, erythromycin and troleandomycin have been identified as inhibitors of the first-pass effect, in addition to any pharmacological effect they possess. These compounds, however, are antiviral, antimicrobial, or antifungal agents. Because of the heightened current awareness of the fact that overuse of such agents can result in resistant microbial strains, because some of the most effective inhibitors are antimicrobials, and because transplant and HIV-infected patients have compromised immune systems, the use of these inhibitors of the first-pass effect has significant drawbacks and, for example, in the case of ketoconazole, the purposeful co-administration of this inhibitor with drugs susceptible to the first-pass effect has not become widespread. In fact, the emergence of antifungal drug resistance in immunocompromised patients is already known (T. J. Walsh: "Emergence of Antifungal Drug Resistance in Immunocompromised Patients" Seminar, National Institutes of Health, Feb. 7, 1996; Georgopapadakou, N. H. et al, Antimicrobial Agents and Chemotherapy, Feb. 1996, p. 279–291).

Dietary supplements, medicines, compounds, extracts, etc. that are based on materials isolated from nature are increasingly being studied and made available to consumers. This trend is largely due to the fact that obtaining patent protection for these materials has become routine (see, for example, U.S. Pat. Nos. 4,708,948, 5,409,938, 5,314,899, 5,591,770 and 5,654,432, all incorporated herein by reference). Not surprisingly, this trend is now spreading to first-pass effective agents.

In 1991, Bailey et al. reported (Bailey, D. G., et al, The Lancet, Vol. 337, Feb. 2, 1991, p. 268, incorporated herein by reference) that grapefruit juice increased the bioavailability of felodipine, and indicated that the inhibition of cytochrome P450 enzymes by bioflavonoids could explain their findings. This identification of bioflavonoids as the active ingredient in grapefruit juice was immediately challenged by R. Chayen et al. (The Lancet, Vol. 337, Apr. 6, 1991, p. 854) who suggested that sesquiterpenoid compounds rather than flavonoids were the active ingredients in grapefruit juice responsible for inhibition of the first-pass effect. Although Bailey and Edgar were granted a patent (U.S. Pat. No. 5,229,116, incorporated herein by reference) directed to a method of increasing the bioavailability of a pharmaceutical agent by co-administration of a flavonoid such as naringin, their own recent work has openly brought into question the accuracy of their initial identification of flavonoids as active ingredient. See, for example, Bailey et al., Clin. Pharmacokinet. 26 (2): 91–98, 1994, particularly pages 95 and 96 thereof. See also Edwards, D. J. et al, Life Sciences, Vol. 59, No. 13, pp. 1025–1030, 1996.

The reported effects of grapefruit juice as an effective inhibitor of the first-pass effect has lead to numerous research articles regarding the inhibition of the first-pass effect by grapefruit juice on, e.g., nifedipine, nitrendipine, nisoldipine, cyclosporin A, midazolam, triazolam, coumarin, and caffeine. As these results have become better known, the so-called "grapefruit juice effect" has become the subject of newspaper articles, newsletters and medical texts intended for the general public. See, for example, "The Medical Letter", Vol. 37 (issue 955) Aug. 18, 1995, *The Peoples Pharmacy*, Chapter 4 (St. Martin's Press) 1996, p. 41, the Feb. 19, 1991 newspaper article regarding felodopine and grapefruit juice in the New York Times (section C, page 3, column 1) and a recent article in the Washington Post (Section A, p. 11, Aug. 30, 1996).

A review of the published studies that demonstrate the grapefruit juice effect also shows that the magnitude of the effect varies widely, and it is the present inventors' suspicion that this variation is traceable to the source of the juice. In fact, the production of commercial citrus juice involves a complicated series of factors that increase the variability of the final product's composition. These factors include the squeezing technique, the concentration technique, the origin of the fruit, the ripeness of the fruit at harvest, the admixture of fruits differing in origin and ripeness, the admixture of juice and fruit tailings, etc. Because the active agents in the grapefruit juice that inhibit the first-pass effect were unknown or misidentified, scientists and consumers could not choose a grapefruit juice preparation and rely upon its utility to inhibit the first-pass effect.

Moreover, grapefruit juice in particular and citrus products in general are known to contain phototoxic furocoumarin derivatives including psoralen, xanthotoxin and bergapten. While these compounds are useful for the controlled, clinical treatment of selected dermatological diseases including vitiligo, psoriasis and mycosis fungoides, they are also known to be toxic, in particular, phototoxic. The structure-activity relationship for the phototoxicity of furocoumarins has been clearly delineated from human studies (for example, L. Musajo et al. Herba Hungarica, 1971, Tom. 10, No. 2–3, pp. 79–94), and these studies show that photosensitizing activity is removed by ring hydroxylation or by lengthening the alkyl-chain length of ether substituents.

Careful evaluation of the literature shows that psoralen and certain low carbon number ether-substituted furocoumarins that are given to humans in large doses do inhibit cytochrome P450. See, for example, D. Bickers et al., J. Investigative Dermatology, 79:201–205, 1982, M. Tinel et al., Biochemical Pharmacology, Vol. 36, No. 6, 951–955, 1987, H. Fouin-Fortunet et al., J. Pharm. Experimental Therapeutics, Vol. 236, No. 1, 237–247, 1986, and D. Mays et al, Clin. Pharmacol. Ther., 42:621–626, 1987. Thus, and because the known successful inhibitors of the first-pass effect generally inhibit cytochrome P450, a tempting conclusion, particularly in view of the recent disclaimers by Bailey, and others, is that these low molecular weight furocoumarins present in citrus are the active first-pass inhibitors in grapefruit juice. In fact, and as will be described more fully below with regard to the present invention, the present inventor has found that this is not the case. Because the present inventor has discovered specific compounds that inhibit the first-pass effect it is now possible to produce a reliable, safe composition that both inhibits the first-pass effect and, if desired, that is citrus-based or of citrus origin and which contains no or reduced amounts of low molecular weight phototoxic furocoumarins.

OBJECTS OF THE PRESENT INVENTION

Figure 1:
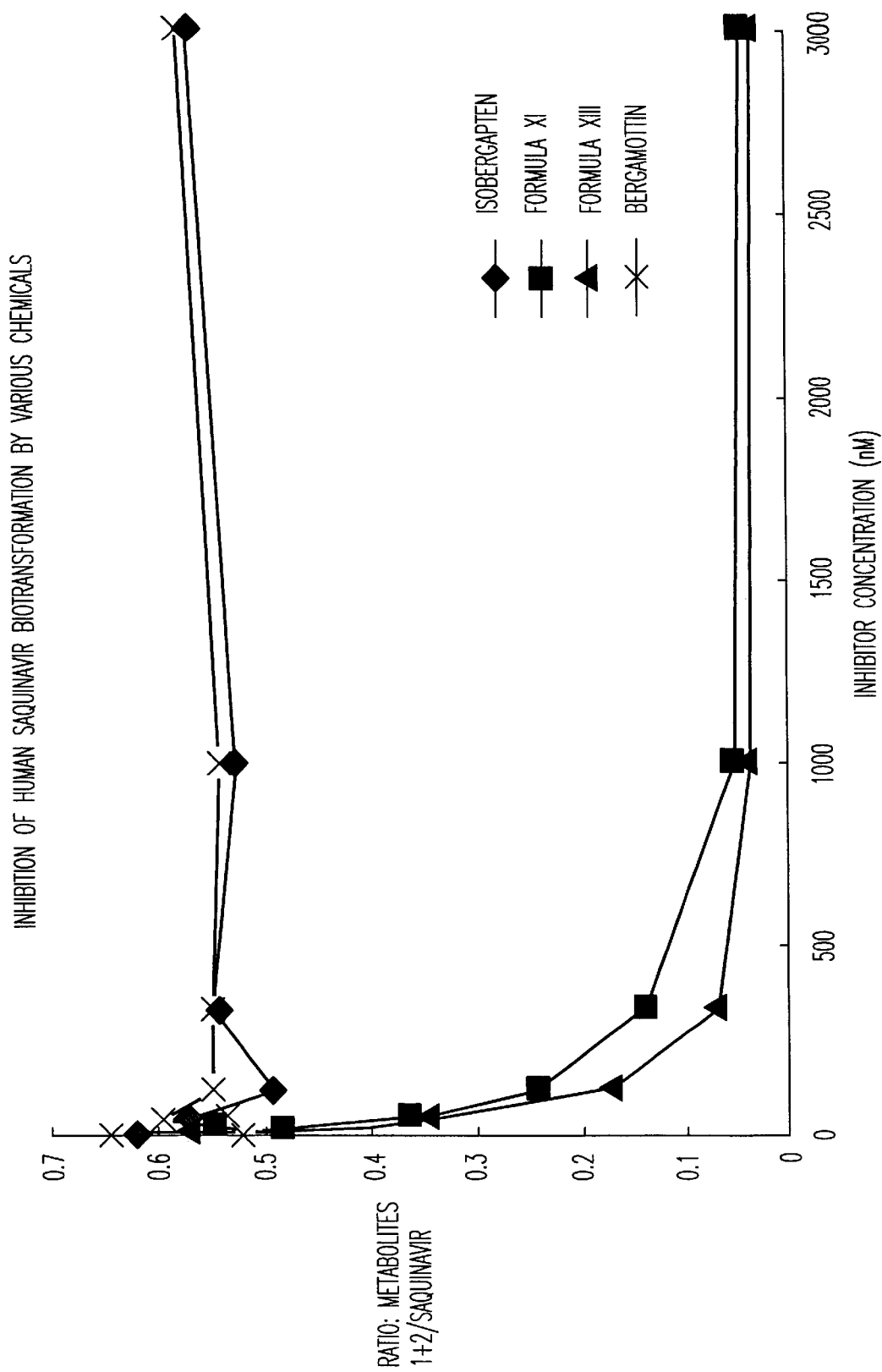
FIG. 1 shows inhibitor results for various inhibitors.

It is one object of this invention to provide chemical compounds and compositions that inhibit the first-pass effect and which are in a form, concentration, purity, etc. other than that which is naturally or commercially occurring.

Another object of the present invention is to provide a reliable, safe citrus-based or citrus-origin product that comprises one or more invention compounds in non-naturally and non-commercially occurring amounts and inhibits the first-pass effect and which, optionally, is free of or contains a reduced amount (as compared to a naturally or commercially occurring amount) of phototoxic and, optionally, non-first-pass inhibiting low molecular weight furocoumarins, which is useful as a food or dietary supplement, a pharmaceutical, a drug, etc.

Another object of the present invention is to provide a composition comprising one or more invention compounds that is effective against the first-pass effect.

Another object of the present invention is to provide a composition that contains one or more of the invention compounds and no or reduced amounts as compared to naturally or commercially occurring amounts of phototoxic low molecular weight furocoumarins.

Another object of the present invention is to provide a composition comprising at least one invention compound and providing consistent and reliable first-pass inhibiting activity.

Another object of the present invention is to provide the above-described compounds and compositions as a component of products and mixtures that provide active ingredients, therapeutic agents, drugs, etc. or other substances that are subject to the first-pass effect in humans.

Another object of the present invention is to provide first-pass effect inhibiting compounds, also called bioenhancers and inhibitors herein, in non-natural and non-commercially occurring forms.

Another object of the present invention is to provide mixtures of one or more invention first-pass effect inhibiting compounds with various therapeutic agents, active agents, drugs or other substances (hereinafter referred to as "drugs") that are subject to the first-pass effect.

Another object of the present invention is a method for inhibiting the first-pass effect in human patients, animals, etc. taking drugs having a first-pass effect.

Another object of the present invention is a method for preparing the above-described compositions, compounds, mixtures, etc.

Another object of the present invention is a method for preparing a citrus-based or citrus-origin composition containing no or reduced amounts as compared to naturally and commercially occurring amounts of phototoxic and non-first-pass inhibiting furocoumarins preferably using reagents that the U.S. Food and Drug Administration regards may be used for food or drug manufacturing, including GRAS materials (in this application, "non-first-pass inhibiting" includes first-pass activity provided by 2000 nM bergamottin or imperatorin according to Protocol C or C' herein).

Another object of the present invention is to provide and use first-pass effective compounds and compositions containing a first pass effective amount (in aggregate or individually) of at least one invention compound in isolated form and/or pyrogen-free form and/or sterile form and/or substantially pure form and/or pharmaceutical form and/or chemically pure form and/or in a form comprising a higher concentration or purity of invention compounds than found both in nature and commercially. As used herein "commercially" means products produced and sold locally, nationally and internationally, especially by the citrus-processing industry. These forms, as their names specify, are different from the invention compounds, as they naturally occur in, for example, commercial citrus and in citrus products such as juice, cold pressed oils, juice concentrates, oils, etc.

Another object of the invention is to provide a method of inhibiting the first-pass effect by administration of at least one invention compound, composition etc. to humans.

These and other objects will become apparent to those of ordinary skill in this art upon a full appreciation of the invention as described below with regard to preferred embodiments.

DETAILED DESCRIPTION OF THE PREFERRED EMBODIMENTS

The present inventor has discovered chemical compounds which inhibit the first-pass effect of orally administered drugs in humans. The present inventor has also discovered that phototoxic low molecular weight furocoumarins and certain ether-substituted furocoumarins that are naturally present in citrus extracts, juices, byproducts, etc. may be removed therefrom or reduced in concentration without destroying the first-pass effect inhibiting compounds therein. The present inventor has also discovered a method for preparing citrus-based compositions using only FDA or USP acceptable reagents. The present invention has been completed on the basis of these findings and will be described in more detail below.

The invention chemical compounds which inhibit the first-pass effect in animals, including humans, are, in one preferred embodiment, compounds according to the following Formulae I–IV:

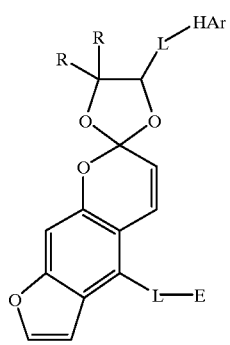

I

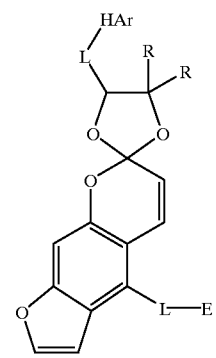

II

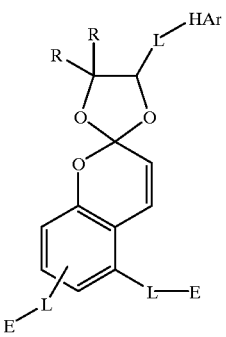

III

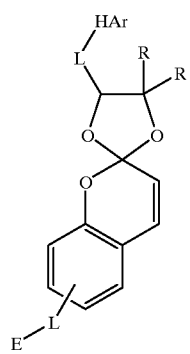

IV

In each of the above structures, R is, independently, H or an optionally substituted $C_1$–$C_{15}$ alkyl group, L is an optionally substituted $C_1$–$C_{15}$ linear or branched, saturated, monounsaturated or polyunsaturated alkyl group optionally interrupted by one or plural nonadjacent sulfur or oxygen atoms and optionally terminated at one or both ends by oxygen, HAr is an optionally substituted $C_6$–$C_{24}$ aromatic group or heteroaromatic group optionally containing one or plural ring atoms selected from the group consisting of N, O, S, and P, and E is —OH, —COOH, —COOR (where R is defined above) or an optionally substituted $C_1$–$C_8$ linear or branched, saturated, monounsaturated or polyunsaturated alkyl group optionally interrupted by one or plural nonadjacent oxygen or sulfur atoms, or E is a $C_3$–$C_8$ optionally substituted cyclic saturated, monounsaturated or polyunsaturated alkyl group optionally interrupted by one or plural nonadjacent oxygen or sulfur atoms, or E is optionally substituted HAr. Preferably, the compounds of Formulae I–IV as well as those described below do not contain a peroxide (0-0) group. Disulfide groups (S-S) are not preferred, but may be present. Preferably E is an epoxide or dihydroxy radical such as —CH(OH)$_2$. E may also be an acid-opened epoxide group.

The compounds of the invention as described above are unlimited with regard to stereochemistry, E-Z isomerism and all possibilities are included. Racemic mixtures are included as are each and every enantiomer and diasteriomer. Preferred stereochemistry is shown later.

The groups R, L, HAr, and E may optionally be substituted with a $C_1$–$C_6$ linear, branched or cyclic alkyl group, —OH, a halogen atom, a $C_1$–$C_5$ alkoxy group, a $C_1$–$C_5$ alkyl carbonyloxy group, a $C_1$–$C_5$ alkoxycarbonyl group, etc. Such substituents also may be optionally substituted directly on the ring structures of Formulae I–IV regardless of whether such substituents appear on R, L, HAr or E.

A second preferred embodiment of the present invention chemical compounds which inhibit the first-pass effect are depicted by Formulae V–X:
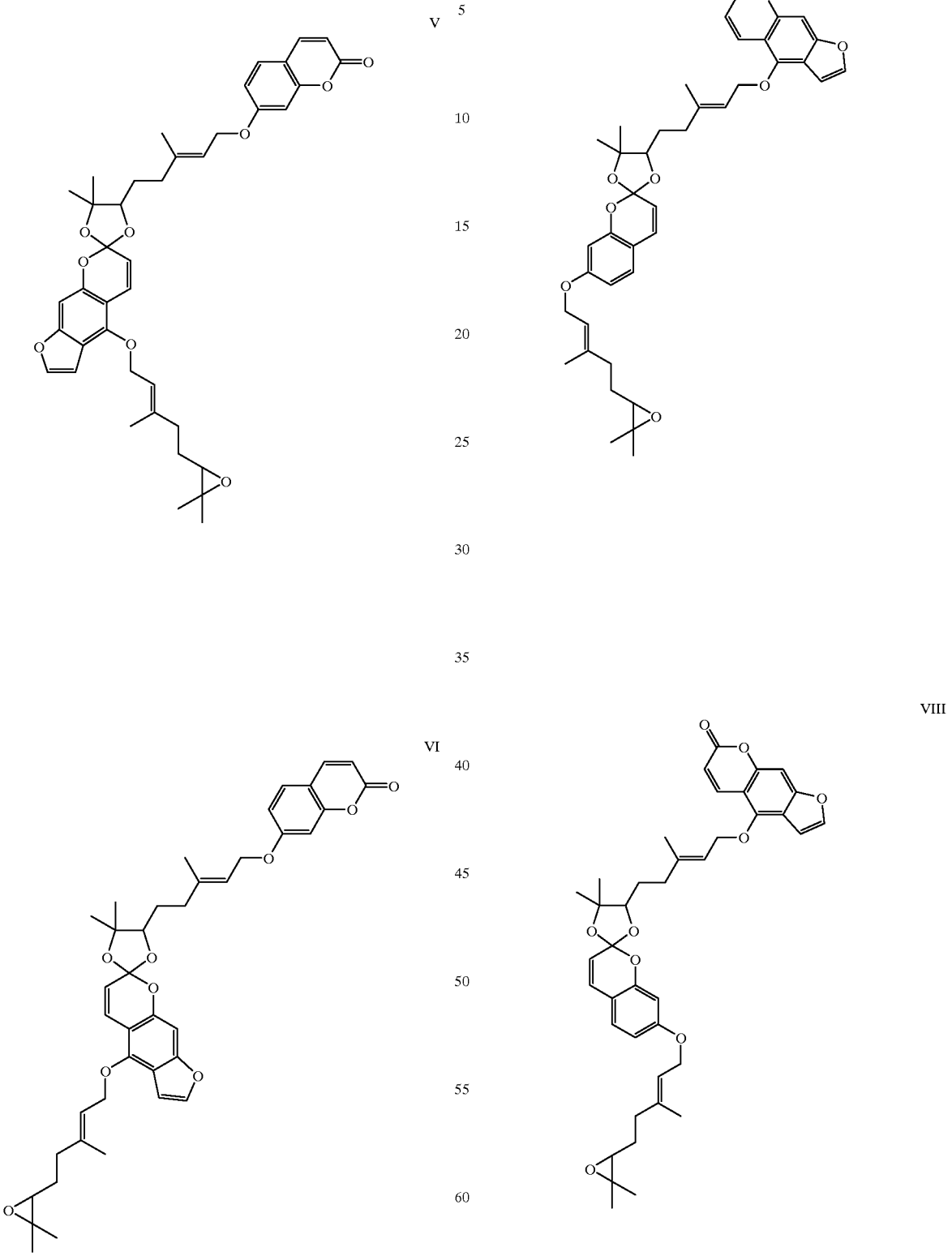

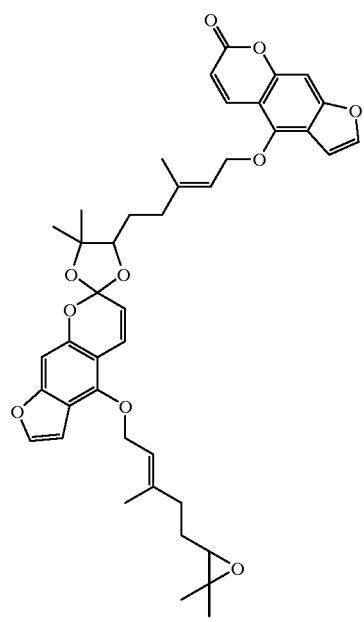
IX
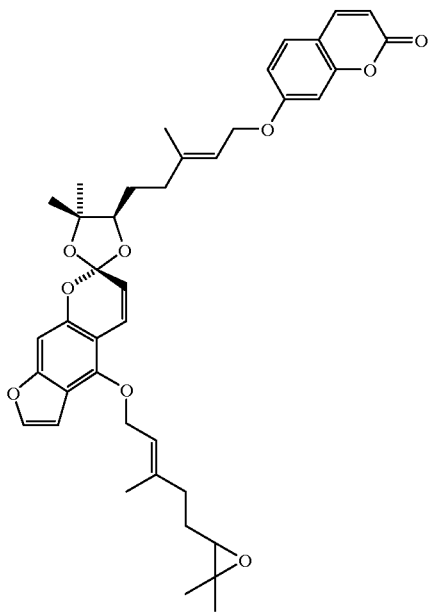
XI
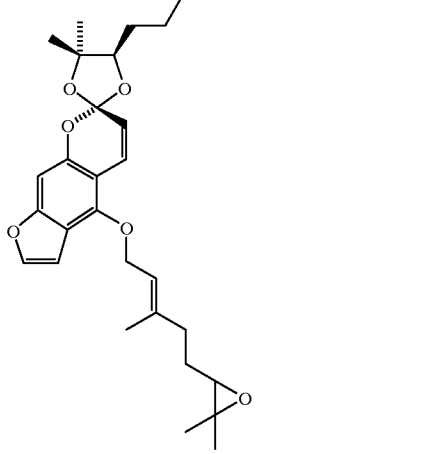
X
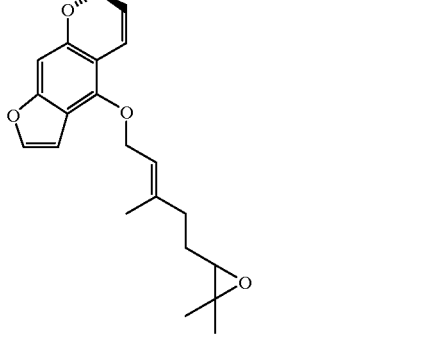
XII
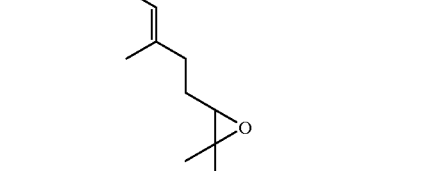
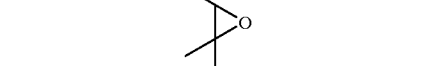
As noted above for Formulae I–IV, Formulae V–X are unlimited with regard to stereochemistry, E-Z isomerism, etc.
The most preferred compounds according to the present invention, which inhibit the first-pass effect, are those according to the second embodiment above and having the following stereochemistry (formulae XI–XVI):

XIII
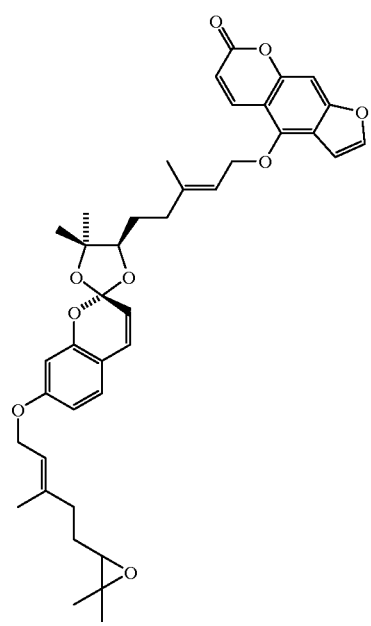
XV
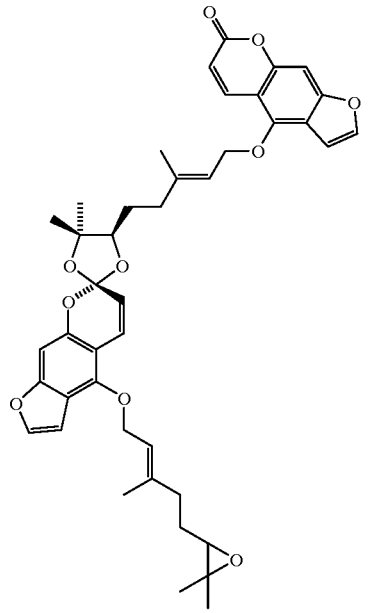
XIV
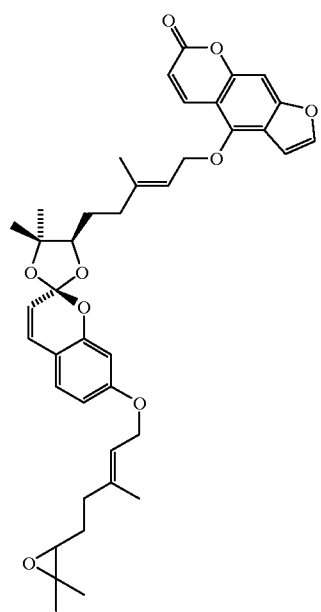
XVI
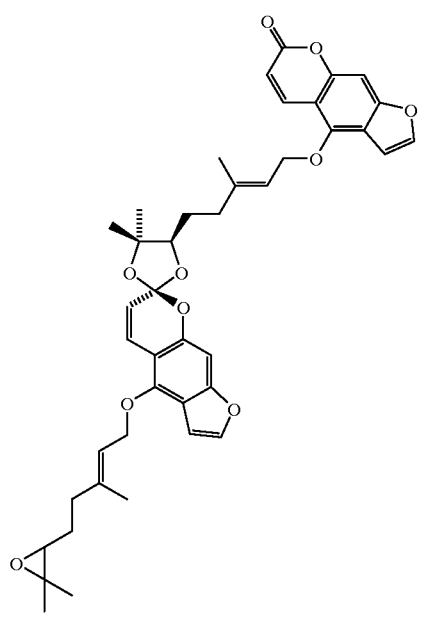

The compositions of the present invention contain at least one invention first-pass effective chemical compound preferably in a first-pass effective amount. Citrus-based compositions of the invention further contain a citrus-derived extract, concentrate, peel, juice, oil, by-product, etc., (hereinafter referred to as the citrus-derived substance) and may be provided by any combination of these forms and may be derived from more than one citrus fruit. Useful citrus fruits herein include grapefruit, lemon, lime and. preferably, any citrus fruit naturally containing an invention first-pass effect inhibiting compound or mixture of such compounds. Prior work in the field indicates that a common type of orange (Citrus sinensis) does not inhibit the first-pass effect. Citrus fruits that contain one or more substances that inhibit the first-pass effect are included in the invention, including all cross breeds, etc. and are referred to herein as "first-pass citrus". A preferred citrus fruit useful in the present invention is grapefruit.

First-pass effective compounds, substances and compositions described herein are materials that prevent or retard the degradation of orally administered drugs in the body. Preferably, the first-pass effective materials of the invention, including substances, compositions, mixtures, invention compounds, etc. increase drug bioavailability by at least 1%, preferably by more than 5% and most preferably by more than 15% including 20, 25, 30, 35, 40, 45, 50, 55, 60, 65, 70, 75, 80, 85, 90, 100, 150, 200, 250, 300, etc. percent as measured by the Area Under the Curve (AUC) method. See U.S. Pat. No. 5,567,592 incorporated herein by reference. A several-fold, including 5, 10, 15, 20-fold, etc. increase in bioavailability (i.e., several hundreds or thousands of percent AUC increase) is not unusual with the present invention. The first-pass effectiveness of invention compounds, composition, mixtures, materials, etc. may also be measured by, and preferably meet the criteria of, the methods and characterizations described in WO 97/15269, U.S. Pat. No. 5,665,386 and PCT/US96/09607, all incorporated herein by reference.

Preferred citrus-derived substances of the invention include cold-pressed citrus oil, particularly cold-pressed grapefruit, lime, lemon, etc., oil, and citrus by-products including tailings from citrus packing/juice plants. Cold-pressed citrus oils, including cold-pressed orange (except Citrus sinensis), grapefruit. lime and lemon oil, are commodities and are described, for example, in the Food Chemicals Codex, Fourth Edition, National Academy Press, Washington, D.C. 1996, incorporated herein by reference. Other citrus-derived substances useful herein include the various other citrus oils (distilled, essential, desert type, etc.), bitter cold-pressed oils, etc. Geographical origin of the invention citrus providing the citrus-derived substance is unimportant herein. Citrus juices or peel (rind) may also be used, as well as any first-pass effective solid, semi-solid or liquid portion of a first-pass citrus. Mixtures may be used.

The citrus-derived substance present in invention compositions may make up the entire citrus-based composition or may be only a part thereof. Thus, if the citrus-based substance is prepared such that it contains one or more compounds according to Formulae I–XVI in a first-pass effective amount no further compound need be added. Food grade or pharmaceutically acceptable diluents, excipients, carriers, etc., may be added, if desired.

The citrus-derived substance of the present invention composition is preferably treated so as to reduce the amount of phototoxic and, optionally, non-first-pass effective, furocoumarins naturally present therein. Preferably, these furocoumarins are completely removed, meaning that they are removed to an extent such that their presence is undetectable by liquid and, preferably, gas chromatography.

The invention method for removing phototoxic low molecular weight furocoumarins from invention citrus-derived components preferably comprises optional removal of volatile components (components removed after 12–48 h at a pressure of $10^{-2}$–$10^{-3}$ Torr) and extraction with mixtures of at least one $C_1$–$C_{10}$ alcohol (preferably ethanol) and water, optionally in the presence of base. In certain situations it is preferable not to remove volatile components such as naturally-occurring terpenes but rather to use these volatiles essentially as solvent in further processing. The extraction mixture of alcohol and water may be discarded and what is left is useful herein. $C_2$–$C_5$ alcohols are also preferred as are $C_2$ and $C_3$ and $C_4$ alcohols. The alcohol (ethanol) may either be 100% alcohol or may be conveniently supplied and used in commonly available alcohol-water dilutions (e.g., 95% ethanol/5% water, etc.). In all cases the alcohol (ethanol) reagent is preferably U.S.P. grade or better. The water used herein for extracting the invention citrus-derived substance (component) is preferably distilled water, and is also preferably U.S.P. grade or better. Any combination of solvents or single solvent may be used herein for extraction. The solvent(s) are preferably FDA acceptable for food and drug manufacturing.

The present invention method for removing phototoxic low molecular weight furocoumarins may include successive extractions with alcohol (ethanol)/water mixtures, and the successive alcohol (ethanol)/water mixtures used may either be of the same volume ratio or different volume ratios. Preferred alcohol (ethanol):water volume ratios range from 1:10–10:1, are more preferably 1:1 (±3%, 5%, 8% or 10%) and may be 20–80 or 45–60% alcohol (ethanol) on a volume/volume basis, and include 2:1, 3:1, 1:2, 1:3, etc. as well as 55/45, 60/40, 65/35, 70/30, 10/90, 15/85, 20/80, 25/75, 30/70, 35/65, 40/60, 45/55, 40/60, 35/65, 30/70, etc. alcohol/water. The extractions may be accomplished by any method known in the art including liquid-liquid extraction, liquid-solid extraction, continuous extraction etc. When the raw material used to prepare the invention citrus-derived extract is, for example, an oil, the alcohol (ethanol)/water mixture used for extraction can be simply added thereto, shaken therewith, and separated naturally or with the help of a centrifuge. Repeated extraction is helpful, as are continuous extraction methods such as countercurrent extraction, etc.

As noted above, base is preferably used in removing phototoxic furocoumarins and may be added to the water or alcohol or both. Preferred bases are the alkali and alkaline earth hydroxides and oxides, most preferably sodium hydroxide and potassium hydroxide. The base is generally present in amounts from 0.01–80 grams per liter of alcohol/water mixture.

Preferably, the invention method for removing phototoxic low molecular weight furocoumarins significantly diminishes, and preferably completely removes beyond the detection limits of liquid and, preferably, gas chromatography, methoxy-substituted linear and angular furocoumarins including xanthotoxin (8-methoxypsoralen), bergapten (5-methoxypsoralen), isobergapten, isopimpinellin, etc., and unsubstituted linear and angular furocoumarins (psoralen, angelicin, etc.). Furocoumarins that have been determined herein to be ineffective first-pass effect furocoumarins may also be removed, if desired. These compounds include bergamottin, psoralen, angelicin, isopimpinellin, marmin, 6', 7'-dihydroxybergamottin, and imperatorin.

The invention citrus-derived substance, invention compositions, invention mixtures, invention pharmaceutical compositions, etc. preferably contain a first-pass effective amount of at least one first-pass effective compound of Formulae I–XVI above. In the alternative, several compounds of Formulae I–XVI may be present, each in non-first-pass effective amounts where the sum of the concentrations of said compounds provides first-pass effectiveness.

In addition to the description above, one or more of the hydrogen atoms depicted in these formulae (i.e., Formulae I–XVI) may be replaced by one or any combination of two or more of hydroxy, halogen, linear or branched $C_1$–$C_{40}$ hydrocarbon, $C_1$–$C_{40}$ linear or branched ether (—OR where R is linear or branched hydrocarbon), $C_1$–$C_{40}$ alkylhydroxy (—ROH where R is linear or branched hydrocarbon and OH is bonded to a primary, secondary or tertiary carbon), etc. As used herein "hydrocarbon" means branched and linear alkyl and branched and linear alkenyl. Alkenyl is any hydrocarbon with at least one double bond but including multiple conjugated and nonconjugated double bonds. All salts, particularly pharmaceutically acceptable salts, and stereoisomers, physical forms, etc. are also included. The compounds described in formulae I–XVI may be synthesized by any general technique known in the art, and their synthesis is within the skill of the ordinary artisan in this field. Now that they have been identified they can also be isolated from a citrus-derived substance as shown herein.

Preferred methods for making the invention compounds of Formulae I–XVI include the following schemes:

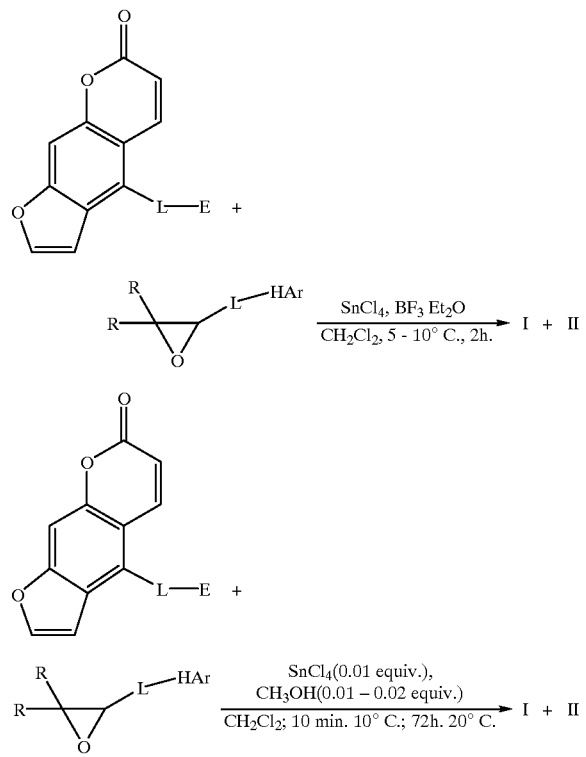

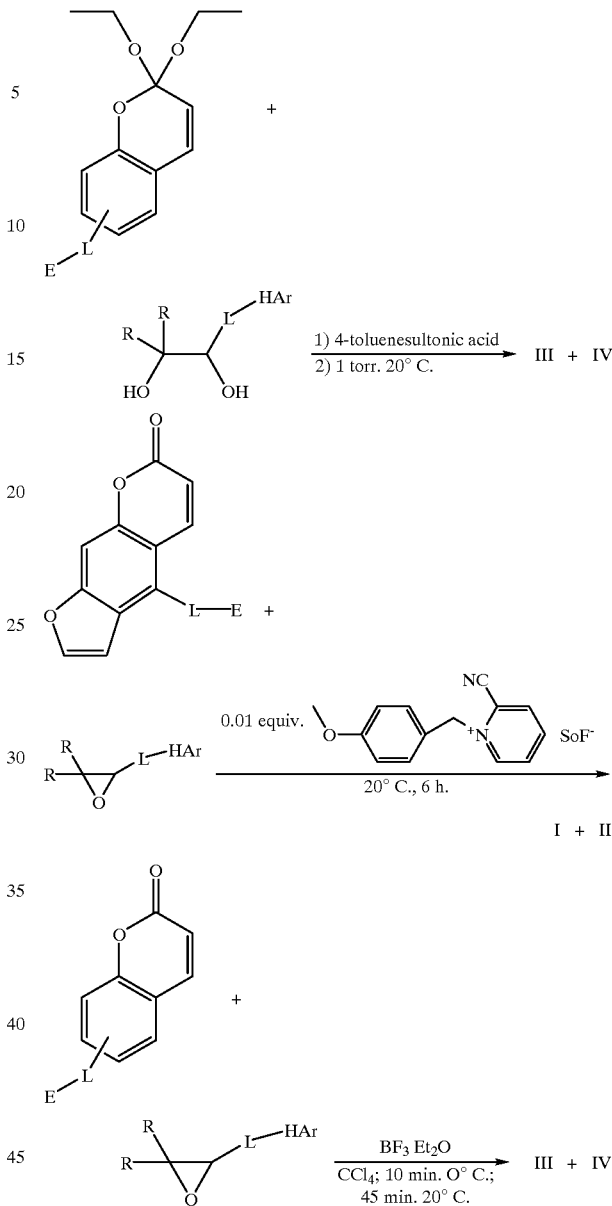

Such reactions are within the skill of the ordinary artisan. See, for example, Chemistry Letters, 2019–2022, 1990, Can. J. Chem., 63: 2673–2678, 1985, Australian Journal of Chemistry, 42: 1235–1248, 1989, East German patent DD 275687 and Soviet Union patent SU 1397449, all incorporated herein by reference. Although each of the reaction schema shown above yield either Formulae I+II or Formulae III+IV, each method can give Formulae I–IV if the appropriate reactants are used. The present invention compounds, citrus-derived substance, mixtures, pharmaceutical compositions, etc. preferably contain at least one compound according to Formulae I–XVI above. Mixtures may be used.

The use of present invention citrus-derived substance, compositions, mixtures, inhibitors, compounds, etc. are not limited and may preferably be administered in amounts of 2 nanograms—2 g and more per patient per day to increase the bioavailability of drugs taken orally by a patient. Compositions of the invention may contain, preferably, more of the invention compounds than naturally present in citrus products. Dosages are determinable by those of ordinary skill in the art and depend upon the extent to which a, e.g., active agent (drug) is subject to the first-pass effect, etc. Dosage forms include oral administration forms, topical administration forms, injection forms. The invention compounds, citrus-derived substance, compositions, mixtures, etc. may optionally be part of or added to a citrus-based composition or other edible material which is preferably a taste-masking flavor, juice, etc.

The citrus-derived substance, mixtures, compositions and compounds of the invention inhibit the first-pass effect of drugs taken orally by humans and other animals. A "first-pass effective amount" of an invention material is any amount that increases the oral bioavailability of any substance by any amount (e.g., 1%, 5%, 10%, etc.; see above where the AUC method is described, including all values and ranges between these values) as compared to the case where no invention material is administered in such a situation. A "first-pass effective" invention citrus-derived substance, mixture, composition or compound is a material that inhibits the observed first-pass effect of at least one drug in an animal, preferably a human, preferably the first-pass effect caused by the cytochrome P450 system. This is also referred to herein as anti-first-pass activity. Administration is preferably co-administration, meaning just before, just after, or with drug, active agent, therapeutic agent, medical food, etc. subject to the first-pass effect. "Just before" and "just after" include all times where the invention material provides a benefit by inhibiting the first-pass effect. Preferred forms of the invention comprise the invention compounds, citrus-derived substance, mixture, composition, etc. inside of, e.g., a gel capsule, or co-formulated with food-grade or pharmaceutically-acceptable binders, diluents, etc. Dosage forms (salt or base, tablet or gum, etc.) as well as binders, salt forms, excipients, etc. which are useful are found in, e.g., U.S. Pat. Nos. 5,576,448, 5,576,446, 5,576,437, 5,576, 439, 5,576,438, 5,576,337, 5,576,339 and 5,576,336, all incorporated herein by reference. The invention citrus-derived substance, mixtures compositions and compounds are preferably provided in an amount that provides consistent, reliable potency from batch to batch regardless of the form in which it is provided.

The word "drug" as used herein is defined as a chemical capable of administration to an organism which modifies or alters the organism's physiology. More preferably the word "drug" as used herein is defined as any substance intended for use in the treatment or prevention of disease, particularly for humans. Drug includes synthetic and naturally occurring toxins and bioaffecting substances as well as recognized pharmaceuticals, such as those listed in Merck Index, Twelfth Ed., Merck Research Laboratories, Whitehouse Station, N.J., 1996, "The Physicians Desk Reference," 47th edition, 1993, pages 101–321; "Goodman and Gilman's The Pharmacological Basis of Therapeutics" 8th Edition (1990), pages 84–1614 and 1655–1715; and "The United States Pharmacopeia, The National Formulary", USP XXII NF XVII (1990), the compounds of these references being herein incorporated by reference. The term drug also includes compounds that have the indicated properties that are not yet discovered or available in the U.S. The term drug includes pro-active, activated and metabolized forms of drugs. The present invention can be used with drugs consisting of charged, uncharged, hydrophilic, zwitter-ionic, or hydrophobic species. as well as any combination of these physical characteristics. A hydrophobic drug is defined as a drug which in its non-ionized form is more soluble in lipid or fat than in water. Preferably, a hydrophobic drug is defined as a drug more soluble in octanol than in water. See U.S. Pat. No. 5,567,592, incorporated herein by reference. The invention can be used with humans and animals such as mammals.

The present invention compounds and citrus-derived substances may be co-formulated with drugs, preferably drugs that are subject to the first-pass effect. Preferably the drug has an oral bioavailability of 92% or less, more preferably 50% or less. Examples include, in addition to those incorporated by reference above, saquinavir, indinavir, L-deprenyl, tacrolimus, cyclosporin A (Sandimmune®), cyclosporin A (Neoral®), nelfinavir, VX-478/141W94, felodipine, nifedipine and sumatriptan. Such co-formulations include the invention citrus-derived substance and/or one or more compounds in amounts mentioned above with, typically, lesser amounts than currently necessary of drug active ingredients that are subject to the first-pass effect. Binders, diluents, etc. acceptable for pharmaceutical use can also be added. One of ordinary skill in the art is capable of determining the dosage of the invention compounds based on simple testing procedures well known in the art and including pharmacological experiments which determine the amount of drug in the blood stream over a given time period after administration.

Other products useful for co-formulation herein are any and all drug, medical food, or other products that are subject to the first-pass effect. Examples of drugs are listed in the Merck Index. Twelfth Ed., Merck Research Laboratories. Whitehouse Station, N.J., 1996, incorporated herein by reference. Determining whether a substance is subject to the first-pass effect is within the skill of the average artisan in this field.

It is preferred that invention materials be protected from stomach acid by, e.g., a coating. Such coatings are well known in the art, and include enteric coatings, etc. See the Kirk-Othmer Encyclopedia of Chemical Technology, 3rd Ed. Vol. 17, p. 281 ff, incorporated herein by reference. Other useful pharmaceutical forms may also be used, such as time-release forms (coatings), hard-and soft-shell gelatin capsules, etc.

EXAMPLES

Synthesis of a Spiro Ortho Ester (Formula XVII)

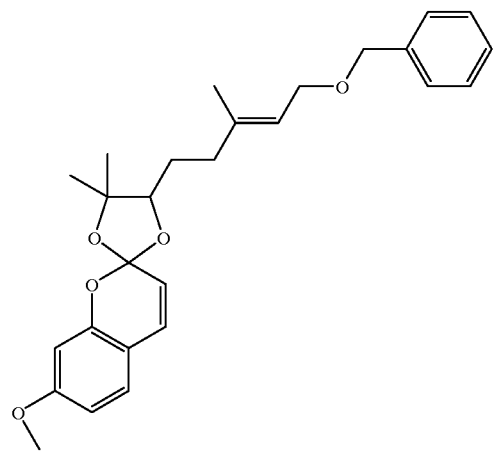

XVII

Benzyl 6,7-epoxygeranyl ether was placed in an evacuated chamber (0.1 torr) overnight in order to remove extraneous water from the sample; 190 mg (730 µmol) was weighed. Three equivalents of 7-methoxycoumarin (0.386 g) was dissolved in 3 mL $CH_2Cl_2$, and this liquid was transferred to a closed glass container. Helium was used to purge the system during the reaction period, the container was maintained at 5–6° C., and the reaction solution was magnetically stirred. Forty-three µL of a 1M solution of $SnCl_4$ in $CH_2Cl_2$ and 16 µmol of $BF_3.Et_2O$ were added; 5 minutes passed, then the epoxide, dissolved in 4 mL $CH_2Cl_2$, was added in 4 equal portions; each portion was followed by 4 µmol $BF_3.Et_2O$. The reaction was held at 5–6° C. and stirred for 3.5 hours, and the reaction apparatus was then disassembled. The reaction mixture was treated immediately as follows: the mixture contains a total of 75 µmol of $BF_3$ and $SnCl_4$, so 3 equivalents of pyridine (225 µmol) were added (reaction mixture held at 5–6° C., with stirring) to destroy the Lewis acid catalysts. After 30 minutes of stirring, the solvent was removed, and the residue was dissolved in 3.16 mL of 95% ethanol; 0.6 mL of 50% KOH in water (w/v) was added, and the solution was mixed vigorously. Water (2.24 mL) was added, and this solution was then placed in a Speed Vac apparatus overnight to remove the ethanol. Approximately 50% of the original volume remained. The aqueous solution was extracted twice with 3 mL $CH_2Cl_2$, and the pooled $CH_2Cl_2$ was extracted twice with 10 mL 5% KOH in water (w/v) and twice with 10 mL 5% NaCl in water (w/v). The $CH_2Cl_2$ was removed, and the residue was dissolved in acetonitrile.

This acetonitrile solution may be used directly for HPLC purification of the spiro ortho ester product via the preferred conditions that follow. Linear gradients were used for elution and were formed by mixing mobile phase A composed of water with mobile phase B composed of acetonitrile (instrument: Hewlett Packard). The elution time, in minutes, as well as the percentage of acetonitrile present in the mixed mobile phase were as follows: 0, 55; 5, 55; 10, 90; 11, 98; 17, 98; 18, 55; 22, 55. The chromatographic column had dimensions of 250 mm length×4.6 mm internal diameter, was packed with C18 bonded to 4 micron silica particles (9% carbon load: YMC, Inc.), was protected with a 23 mm length×4 mm internal diameter column containing the same material and with a 0.5 micron filter, and was maintained at 40±0.2° C. The flow rate was maintained at 1.0 mL/min during the 22 min run cycle. The column eluate from each 10 µL injection was monitored at 259±2 and was fractionated using a robotic collector (Gilson). The retention time of Formula XVII in this system was 13.4 minutes. $^1$H N.M.R. δ(400 MHZ, $CD_3OD$) 1.15, s and 1.26, s and 1.39, s, 4'-Me (diasteriomers); 1.64, s, 8'-Me; 1.6–1.9, m, H6',6'; 2.0–2.3, m, H7'; 3.70, s, 7-OMe; 3.83. m and 4.20, t, H5' (diasteriomers); 4.01, d, H10'; 4.45, s, H12'; 5.39, t, H9'; 5.45, d, H3; 6.40, s, H8; 6.49, d, H6; 6.71, d, H4; 7.06, d, H5; 7.20–7.35, m, phenyl. Mass spectrum m/z (electrospray): MS, 437 ($MH^+$); MS/MS, 261, 177, 153 (fragments of $MH^+$).

Bulk Pretreatment of Cold-pressed Grapefruit Oil for Subsequent Fractionation by Reversed-phase HPLC 1. Prepare 1:1 ethanol:water (v/v) containing 12.5 g KOH/L using denatured reagent alcohol.

2. Mix 1.0 L of cold-pressed grapefruit oil and 330 mL of the basic ethanolic solution in a 2 L separatory funnel for 2.0 min.

3. Wait 5.0 min, then remove the bottom ethanolic phase from the funnel.

4. Repeat steps 2 & 3 four times using fresh 330-mL portions of the basic ethanolic solution.

5. Repeat steps 2 & 3 once using a 330-mL portion of: 1:1 ethanol:water that is prepared without KOH. When KOH is absent, a several-hours wait is required (preferably overnight) in order for the phases to clearly separate. Assessment of the bottom ethanolic phase with pH paper should show that the solution pH is near neutral (≡6, in most cases).

6. Place the oil phase (yield should be greater than 0.9 L) in a vacuum chamber and place the system under vacuum (0.5 torr or better) for 3–4 days. The process is complete when swirling the viscous liquid while under vacuum no longer initiates boiling.

7. Wash the nonvolatile material with portions of acetonitrile, to a total of 200 mL, and separate the acetonitrile-soluble and -insoluble materials by centrifugation (5 min at speed 50, IEC model K2).

8. Remove the acetonitrile from the acetonitrile-soluble phase (step 7) using a Speed Vac apparatus, and weigh the residue (22–25 g would be expected).

9. Add acetonitrile to the residue such that each 5-mL portion contains 1.5 grams of residue, and divide the solution into 5-mL portions.

10. Add 15-mL of iso-octane to each 5-mL portion, cap, vortex mix, and centrifuge the mixture (2 min at speed 35). Discard the top iso-octane phase.

11. Repeat step 10 nine times; acetonitrile should be added occasionally to insure that the bottom phase volume approximates 5 mL.

12. Remove the acetonitrile from the bottom phase (step 11) using a Speed Vac apparatus, and weigh the residue (approximately 20% of the original weight {step 8} would be expected).

13. Dissolve the residue (step 12) in acetonitrile such that a 0.25–0.30 g/mL solution is established, filter the solution through a 0.2 µm Teflon cartridge, and store the solution at −20° C.

Bulk Pretreatment of Cold-pressed Grapefruit Oil for Further use as Dietary Food Supplement, Drug, conFormulation Ingredient, etc.

1. Prepare a 70:30 water:ethanol solution (v/v) that contains 5% potassium hydroxide (w/v) using USP-grade ethanol, NF/FCC-grade KOH, and purified water.

2. Mix the ethanolic solution prepared in step 1 with an equivalent volume (or slight excess) of whole, untreated cold-pressed grapefruit oil (Food Chemicals Codex grade), and transfer the mixture to a heat-and pressure-resistant food-grade container.

3. The sealed container is maintained at 95–100° C. for 1 hour. The container is cooled, the ethanolic phase (lower phase of two-phase system) is removed, and a fresh portion of ethanolic solution (equivalent to the volume used in step 2) is added.

4. Repeat the boiling cycle (step 3) until the desired degree of sample purity is achieved. Ten cycles will remove >99% of polar coumarins and furocoumarins, will remove >90% of prominent nonpolar coumarins and furocoumarins (i.e., epoxyaurapten, epoxybergamottin), and will not appreciably decrease the content of the inhibitory spiro ortho esters.

5. Wash the oil with purified water until the discarded wash water pH becomes neutral.

6. Place the oil phase under vacuum (0.1–0.3 torr) until volatile materials are no longer removed from the sample (as assessed by, for example, inspection of an empty in-line trap maintained at −60 to −90° C.). In general, approximately 95% of the volume of the sample will be removed in this step.

7. Mix the product of step 6 with an equivalent volume of USP ethanol, and centrifuge the mixture. Repeat until the bottom phase is substantially free of spiro ortho ester inhibitors. This method removes ethanol-insoluble materials from the oil novolatile preparation.

8. Optionally, but preferably, place the pooled ethanol extracts from step 7 under vacuum until the ethanol has been substantially removed (e.g., 99%) or reduced (e.g. 10%).

Because adulteration of raw materials is known in the food, flavor, and fragrance industries, citrus-derived components of the invention including cold-pressed citrus oils should preferably be assessed before they are used further in the production of, e.g., compositions of dietary supplements containing a first-pass effective amount of one or a mixture of compounds of Formulae I–XVI. One strategy consists of sample preparation (Protocol A; Protocol A'), followed by chromatography (Protocol B; Protocol B'; Protocol B"), and ending with comparisons to historical standards. Such assessment can provide consistent batches.

The following protocols are useful in preparing various embodiments of the invention.

Protocol A: Preparation of Citrus Oils for Further Chromatographic Processing or for Administration to Humans by Removal of Toxic, Low Molecular Weight Furocoumarins A volume of cold-pressed citrus oil (Food Chemicals Codex grade) was transferred to a container, and all volatile materials were removed. Although several methods exist for removing volatiles (e.g., distillation, distillation under reduced pressure, evaporation under ambient conditions), the preferred method uses Speed Vac concentrators (Savant Instruments; process requires 12–24 h and pressures of $10^{-2}$–$10^{-3}$ torr, and the system is run without added heat) because this method is gentle and expedient. The nonvolatile product yield is generally 0.04 to 0.1 times the initial volume and is a viscous liquid.

Low molecular weight, phototoxic furocoumarins were removed from the nonvolatile preparation by liquid-liquid extraction: 16 times the volume of viscous liquid of 1:1 ethanol:water (v/v; each U.S.P. grade) were added to the nonvolatile preparation, the container capped, the solution mixed vigorously, the container centrifuged (International Equipment Company, Model K-2, 5 min at setting 35), and the top ethanolic phase discarded. The extraction was repeated twice. Extraneous water and ethanol may be removed from the preparation if desired by use, e.g., of a Speed Vac apparatus. The product of this process may be used for human administration in, e.g., filled capsules.

Protocol A': Pretreatment of Citrus Oils Prior to Chromatography

Most citrus oils are not directly suitable for long-term preparative high pressure liquid chromatography because of the substantial presence of materials that show poor solubility in the preferred mobile phase systems. Hence the sample preparation protocol that follows is used prior to chromatography.

Cold-pressed citrus oil (Food Chemicals Codex grade) is transferred to a suitable container, and all volatile materials are removed under reduced pressure ($10^{-2}$–$10^{-3}$ torr, 3–4 days). The nonvolatile product yield is generally only 5–10% of the original volume. The citrus nonvolatiles are mixed with acetonitrile in a ratio of 2:1 (w/w), the mixture is centrifuged (International Equipment Company, Model K-2, 5 min at setting 35), and the upper acetonitrile-containing phase is removed. The extraction with acetonitrile is repeated once, the lower phase is discarded, the first and second acetonitrile phases are pooled, and acetonitrile is removed using Speed Vac concentrators (Savant Instruments; 12 h at $10^{-2}$–$10^{-3}$ torr, without added heat). The nonvolatile material is mixed with ethanolic base (1:1 ethanol:water {v/v; each U.S.P. grade} containing 12.5 g potassium hydroxide/L) in a ratio of 1:4 (w/v), the mixture is centrifuged for 5 min at setting 35, and the upper ethanolic phase is removed and discarded. The nonvolatile material is washed an additional nine times with ethanolic base and, then, once with 1:1 ethanol:water (v/v). The residue that remains is extracted twice with sufficient volumes of acetonitrile such that all colored material is removed. The acetonitrile solution is washed six times with two volumes of hexane or iso-octane, with each hexane extract (upper layer) being removed and discarded, and the resulting acetonitrile solution is filtered through a 0.2 micron Teflon® membrane and evaporated to dryness using a Speed Vac concentrator.

The final product of the above process should appear as a viscous, deep red oil, but seasonal variations in the starting material (citrus oils) apparently can change the quality and appearance of the product of the above process. Hence, if a copious orange crystalline material contaminates the deep red oil, then the number of additional washes with ethanolic base should be increased from nine to nineteen.

Protocol B: Chromatography Methods for Processed Citrus Oils

The product of the above Protocol A is not suitable for any high pressure liquid chromatography because of the substantial presence of materials that are not soluble in the preferred mobile phase systems. Hence the sample preparation protocol that follows is used prior to chromatography. One volume of the product of Protocol A is mixed with four volumes of acetonitrile, the container is capped, the solution is mixed vigorously, the container is centrifuged (5 min at setting 35), and the top acetonitrile layer is filtered through a 0.22 micron Teflon® membrane. The filtered solution is stored in a closed container at −20° C. for 2 days or more and then is passed through filter paper while cold to remove a copious precipitate. The precipitation and filtration step is repeated once. The volume of the acetonitrile solution is noted, and the acetonitrile is removed using a Speed Vac apparatus. The residue is dissolved in half the original volume of acetonitrile, taking care not to disturb any crystalline precipitate, and the solution may now be used for HPLC assessment.

If preparative fractionation of the washed nonvolatile portion of citrus oil is desired, then the HPLC conditions given below are preferred. Linear gradients are used for elution and are formed by mixing mobile phase A composed of water with mobile phase B composed of acetonitrile (instrument: Hewlett Packard). The elution time, in minutes, as well as the percentage of acetonitrile present in the mixed mobile phase are as follows: 0, 75; 5, 75; 10, 90; 11, 98; 17, 98; 18, 75; 22, 75. The chromatographic column has dimensions of 250 mm length×4.6 mm internal diameter, is packed with C18 bonded to 4 micron silica particles (9% carbon load; ODS-L80, YMC, Inc.), is protected with a 23 mm length×4 mm internal diameter column containing the same material and with a 0.5 micron filter, and is maintained at 40+/−0.2° C. The flow rate is maintained at 1.0 mL/min during the 22 min run cycle. The column eluate from each 25 uL injection is monitored at 400+/−200 nm and at 310+/−2 nm and is fractionated using a robotic collector (Gilson).

If qualitative or quantitative assessments of citrus oils, fractions thereof, or reference standards are desired, then the HPLC conditions given below are preferred. Linear gradients are used for elution and are formed by mixing mobile phase A composed of water with mobile phase B composed of acetonitrile (instrument: Hewlett Packard). The elution time, in minutes, as well as the percentage of acetonitrile present in the mixed mobile phase are as follows: 0, 10; 5, 10; 30, 80; 40, 80; 41, 95; 50, 95; 53, 10; 60, 10. The chromatographic column has dimensions of 150 mm length× 2.0 mm internal diameter, is packed with C18 bonded to 4 micron silica particles (14% carbon load; ODS-M80, YMC, Inc.), is protected with a 2 mm internal diameter column packed with a proprietary material (Prism, Keystone Scientific, Inc.) and with a PTFE filter, and is maintained at 35+/−0.2° C. The flow rate is maintained at 0.20 mL/min during the 60 min run cycle. The column eluate from each 10 uL injection is monitored for absorbance at 400+/−200 nm and at 310+/−2 nm and for fluorescence with excitation at 229 nm, emission at 450 nm, and bandpass filtration at 370 nm.

Protocol B': Chromatography Methods for Processed Citrus Oils

If preparative fractionation of the washed nonvolatile portion of citrus oil (product of Protocol A') is desired, then the HPLC conditions given below are preferred. Linear gradients are used for elution and are formed by mixing mobile phase A composed of water with mobile phase B composed of acetonitrile (instrument: Hewlett Packard). The elution time, in minutes, as well as the percentage of acetonitrile present in the mixed mobile phase are as follows: 0, 75; 5, 75; 10, 90; 11, 98; 17, 98; 18, 75; 22, 75. The chromatographic column has dimensions of 250 mm length× 4.6 mm internal diameter, is packed with C18 bonded to 4 micron silica particles (9% carbon load; ODS-L80 YMC, Inc.), is protected with a 23 mm length×4 mm internal diameter column containing the same material and with a 0.5 micron filter, and is maintained at 40+/−0.2° C. The flow rate is maintained at 1.0 mL/min during the 22 min run cycle. The column eluate from each 25 uL injection of acetonitrile solution obtained by Protocol A'is monitored at 400+/−200 nm and at 310+/−2 nm and is fractionated using a robotic collector (Gilson).

If qualitative or quantitative assessments of citrus oils, fractions thereof, or reference standards are desired, then the HPLC conditions given below are preferred. Linear gradients are used for elution and are formed by mixing mobile phase A composed of water with mobile phase B composed of acetonitrile (instrument: Hewlett Packard). The elution time, in minutes, as well as the percentage of acetonitrile present in the mixed mobile phase are as follows: 0, 10; 5, 10; 30, 80; 40, 80; 41, 95; 50, 95; 53, 10; 60, 10. The chromatographic column has dimensions of 150 mm length× 2.0 mm internal diameter, is packed with C18 bonded to 4 micron silica particles (14% carbon load; ODS-M80, YMC, Inc.), is protected with a 2 mm internal diameter guard column packed with a proprietary material (Prism, Keystone Scientific, Inc.) and with a PTFE filter, and is maintained at 35+/−0.2° C. The flow rate is maintained at 0.20 mL/min during the 60 min run cycle. The column eluate from each 10 uL injection is monitored for absorbance at 400+/−200 run and at 310+/−2 nm and for fluorescence with excitation at 229 nm, emission at 450 nm, and bandpass filtration at 370 nm.

Protocol B'': Purification of Invention Compounds Using a Chiral HPLC Column

Pooled residues that result from fractionation of the 11–12.5 min region (Protocol B or B') and solvent removal (Speed Vac, no heat added) are subjected to chiral liquid chromatography. Isocratic elution is employed (mobile phase consists of 3.4 L iso-octane, 0.6 L 95% ethanol {remainder is water}, and 0.2 L isopropanol) to elute Inhibitors XI–XVI from the column (250×4.6 mm, Keystone Scientific, Inc., Chiral from each 25 uL injection (residue is dissolved in mobile phase) is monitored at 400+/−200 nm and at 310+/−2 nm and is fractionated using a robotic collector (Gilson).

Protocol C: Assessment of Human Cytochrome P450-mediated Biotransformation

The process of preparing incubation mixtures begins by mixing 10 uL of ethanol or an ethanolic solution containing an inhibitor with 100 uL of 100 mg/mL bovine serum albumin (Sigma) dissolved in reaction buffer at room temperature. Reaction buffer is composed of 0.10 M sodium phosphate, 1.0 mM ethylenediaminetetraacetic acid, and 5.0 mM magnesium chloride, pH 7.4 (all reagents: Fisher Scientific). Inhibitory chemicals used were ketoconazole (Research Diagnostics, Inc.), miconazole, bergapten, xanthotoxin (previous three from Sigma), bergamotin, imperatorin, isopimpinellin, psoralen, angelicin (previous five from Indofine Chemical Company, Inc.), and fractions or precipitates resulting from Protocols A, A', B, B', or B'' above. When possible, final inhibitor concentrations were expressed in molarity by calculation from the weighed material or by interpolation from HPLC calibration curves prepared with reference materials; otherwise, concentrations are expressed as weight per volume. Reaction tubes are placed on ice in preparation for the manipulations that follow. Sufficient reaction buffer is added so that the final volume of each tube will be 500 uL, 5 uL of a 100-fold concentrate for generating reduced nicotinamide adenine dinucleotide phosphate is added (such that completed reaction mixture contains 1.0 mM nicotinamide adenine dinucleotide phosphate, 1 U/mL glucose-6-phosphate dehydrogenase, and 10 mM glucose-6-phosphate: all from Sigma), and then human hepatic S9 (Anatomic Gift Foundation) is thawed and added in sufficient amounts to cause readily detectable amounts of metabolites to be formed in control reactions (amount necessary varies among individuals, but 10 uL is typical). Reactions are pre-incubated for 3 min at 37° C. in a Dubnoff-type water bath, the reaction mixture is completed by the addition of 10 uL of 100 uM terfenadine (Sigma) dissolved in 1:1 acetonitrile-:water and by gentle mixing, the samples are incubated for 15 min at 37° C., and the reaction is stopped by placing the tube on ice and adding 2.5 mL of 300 nM terfenadine-related compound A (internal standard; U. S. Pharmacopeia) dissolved in acetonitrile.

The samples prepared above are readied for HPLC assessment using the protocol that follows. Each tube is vortex mixed and centrifuged for 10 min at setting 35, the resulting supernatant is transferred to a clean tube, and the liquid is evaporated using a Speed Vac apparatus. The residue in each tube is first dissolved in 40 uL 1:1 acetonitrile:water, 2.5 mL of acetonitrile is added, and the centrifuge-transfer-evaporate step just described is repeated.

The dry residue resulting from the above-described experiments and sample preparation protocol may be analyzed for terfenadine metabolites using the HPLC method described below and may also be used to quantitate the inhibitory chemicals that were added to the reaction (see Protocols B and B'). Linear gradients are used for elution and are formed by mixing mobile phase A composed of water with mobile phase B composed of 0.025% (v/v) formic acid in acetonitrile (instrument: Hewlett Packard). The elution time, in minutes, the percentage of mobile phase B present in the mixed mobile phase and the flow rate (mL/min) are as follows: 0, 10, 0.10; 2, 10, 0.10; 3.5, 10, 0.20; 4, 10, 0.25; 5, 10, 0.25; 30, 55, 0.25; 32, 98, 0.25; 33, 98, 0.40; 39.8, 98, 0.40; 40, 98, 0.25; 45, 10, 0.25; 45.25, 10, 0.20; 50, 10, 0.20; 50.25, 10, 0.10. The chromatographic column has dimensions of 150 mm length×2.1 mm internal diameter, is packed with a proprietary material (Prism, Keystone Scientific, Inc.), is protected with a 2 mm internal diameter column containing the same material and with a PTFE filter, and is maintained at 35+/−0.2° C. The dry sample residue is mixed with 60 uL of 1:1 acetonitrile:water followed by 40 uL water just prior to each 50.25 min run cycle. The column eluate from each 10 uL injection is monitored for fluorescence with excitation at 228 nm, emission at 291 nm, and bandpass filtration at 280 nm. Under these conditions, the retention times of terfenadine alcohol metabolite, terfenadine carboxylic acid metabolite, and the internal standard are 16.2 min, 17.4 min, and 22.2 min, respectively.

Protocol C': Assessment of Human Cytochrome P450-mediated Biotransformation

The process of preparing incubation mixtures begins by mixing 10 uL of ethanol (control reactions) or an ethanolic solution containing an inhibitor with 100 uL of 100 mg/mL bovine serum albumin (Sigma) dissolved in reaction buffer at room temperature. Reaction buffer is composed of 0.10 M sodium phosphate, 1.0 mM ethylenediaminetetraacetic acid, and 5.0 mM magnesium chloride, pH 7.4 (all reagents: Fisher Scientific). Inhibitory chemicals used are ketoconazole (Research Diagnostics, Inc.), ritonavir (Norvir™, Abbott Laboratories), inhibitory chemicals described in Protocol C, and fractions resulting from Protocol B" above. Final inhibitor concentrations were expressed in molarity by calculation from the weighed material or by use of Beer's law. Reaction tubes are placed on ice in preparation for the manipulations that follow. Sufficient reaction buffer is added so that the final volume of each tube will be 500 uL, 5 uL of a 100-fold concentrate for generating reduced nicotinamide adenine dinucleotide phosphate is added (such that completed reaction mixture contains 1.0 mM nicotinamide adenine dinucleotide phosphate, 1 U/mL glucose-6-phosphate dehydrogenase, and 10 mM glucose-6-phosphate; all from Sigma), and then human hepatic S9 (Anatomic Gift Foundation) is thawed and added in sufficient amounts to cause readily detectable amounts of metabolites to be formed in control reactions (amount necessary varies among individuals, but 10 uL is typical). Reactions are pre-incubated for 3 min at 37° C. in a Dubnoff-type water bath, the reaction mixture is completed by the addition of 10 uL of 500 uM saquinavir (Invirase™, Roche Laboratories) dissolved in 1:1 ethanol:water and by gentle mixing, the samples are incubated for 15 min at 37° C., and the reaction is stopped by placing the tube on ice and adding 2.5 mL of acetonitrile.

The samples prepared above are readied for HPLC assessment using the protocol that follows. Each tube is vortex mixed and centrifuged for 10 min at setting 35, the resulting supernatant is transferred to a clean tube, and the liquid is evaporated using a Speed Vac apparatus. The residue in each tube is first dissolved in 40 uL 1:1 acetonitrile:water, 2.5 mL of acetonitrile is added, and the centrifuge-transfer-evaporate step just described is repeated.

The dry residue resulting from the above-described experiments and sample preparation protocol may be analyzed for saquinavir and saquinavir metabolites using the HPLC method described below and may also be used to quantitate the inhibitory chemicals that were added to the reaction (see Protocols B and B'). Linear gradients are used for elution and are formed by mixing mobile phase A composed of water with mobile phase B composed of acetonitrile (instrument: Hewlett Packard). The elution time, in minutes, and the percentage of mobile phase B present in the mixed mobile phase are as follows: 0, 10; 5, 10; 30, 80; 31, 95; 40, 95; 43, 10; 48, 10. The flow rate is 0.2 mL/min throughout the run. The chromatographic column has dimensions of 150 mm length×2.1 mm internal diameter, is packed with a proprietary material (Prism. Keystone Scientific, Inc.), is protected with a 2 mm internal diameter column containing the same material and with a PTFE filter, and is maintained at 35+/−0.2° C. In order to minimize the degradation of analytes, the dry sample residue is mixed with 50 uL of 1:1 acetonitrile:water just prior to each 48 min run cycle. The column eluate from each 10 uL injection is monitored for absorbance at 239+/−2 nm. Under these conditions, the retention times of saquinavir principal metabolite A, saquinavir principal metabolite B. and saquinavir are 24.2 min, 26.0 min, and 30.0 min, respectively.

Demonstration of Effectiveness

Figure 2:
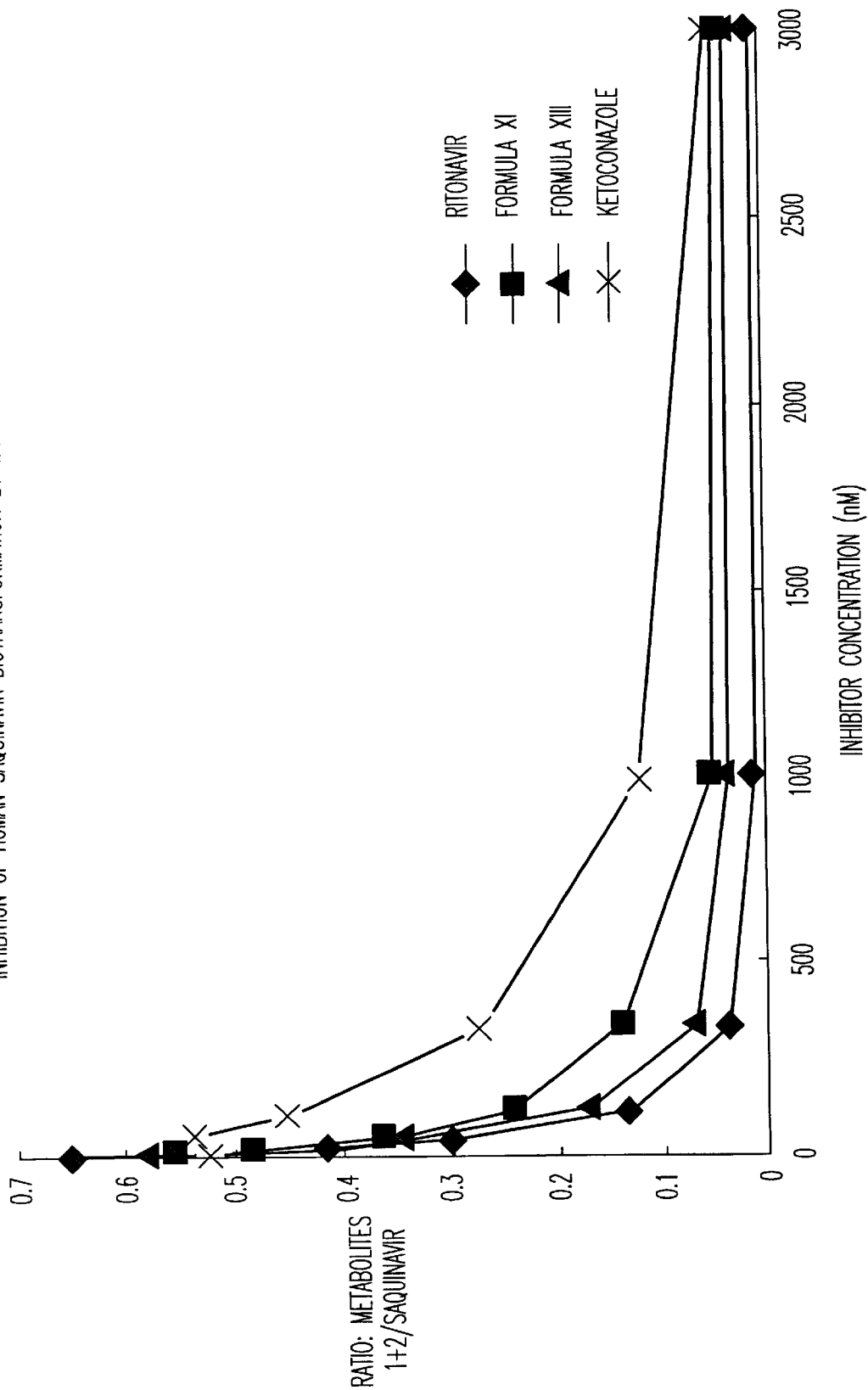
FIG. 2 shows inhibitor results for various inhibitors.

In order to demonstrate the first-pass effectiveness of the present invention, experiments with invention compounds and invention citrus-derived substances were conducted according to Protocol C' above where generation of saquinavir metabolites were measured in the presence of various concentrations of inhibitor. Citrus-derived substances according to the present invention were prepared according to Protocols A', B', and B" above and were compared to known inhibitor Ketoconazole. FIG. 1 shows results for invention compounds of Formulae XI and XIII and also shows that bergamottin and imperatorin are essentially ineffective first-pass inhibitors. FIG. 2 shows how invention compounds compare to known inhibitors Ritonavir and Ketoconazole.

In the invention compounds it is preferred that the furan ring position of the furocoumarin rings be completely free of substitution.

With regard to purification and processing methods, the following embodiments are preferred:

A. A method for processing citrus and selectively removing phototoxic furocoumarins from a first-pass effective citrus-derived substance, comprising the step of extracting said citrus-derived substance with a mixture of at least one $C_2$–$C_4$ alcohol, water, and optionally base, said first-pass effective citrus-derived substance maintaining anti-first-pass activity after said extraction.

B. The method of embodiment A, wherein said citrus-derived substance is a cold-pressed citrus oil.

C. The method of embodiment A, wherein said mixture of ethanol and water is a 30/70 volume/volume mixture of ethanol and water optionally containing 1–10% potassium hydroxide (W/V).

Other preferred embodiments include:

D. A first-pass effective citrus-derived substance which has been extracted with a mixture of at least one $C_2$–$C_4$ alcohol and water so as to reduce the amount of phototoxic furocoumarins therein.

E. The citrus-derived substance of embodiment D, wherein said substance is a cold-pressed citrus oil.

F. The citrus-derived substance of embodiment D, which has been extracted with a 30/70 volume/volume mixture of ethanol and water optionally containing 1–10% potassium hydroxide (W/V).

G. A method for inhibiting the first-pass-effect of a material taken orally by a patient which is subject to the first-pass effect, comprising the step of co-administering to said patient the first-pass effective citrus-derived substance of embodiments A and D.

Invention compositions preferably comprise invention inhibitor material (compound, etc.) (e.g., alone, mixed with drug(s), and/or diluent(s) and/or carrier(s) etc.) such that they inhibit saquinavir biotransformation according to Protocol C' above better than pure ketoconazole on an equal molar (preferred) or weight concentration basis. Alternatively, invention compounds, compositions, mixtures, formulations, etc. (materials) preferably provide a Y-axis value in Protocol C' (see FIG. 1) of less than 0.5, preferably 0.45, 0.4, 0.35, 0.3, 0.25, 0.22, 0.2, 0.18, 0.15, 0.12, 0.1, 0.08, 0.05 or 0.03 or less when 0.01–0.25 mg, including 0.02, 0.04, 0.06, 0.08, 0.1, 0.12, 0.14, 0.16, 0.18, 0.2, 0.22 and 0.24, and all ranges between all values, of invention material is diluted or dissolved to one liter.

A commercial form of citrus containing the invention compounds is cold-pressed grapefruit oil, which has a total concentration of compounds of Formulae XI–XVI in the range of perhaps up to 0.15–0.25 mg/ml. The six compounds are distributed as: XI+XII+XIII+XIV equals approximately 50%, with XV and XVI the remainder. For XI–XIV the distribution is about 3:2:2:1, respectively and about 2:1 for XV:XVI. Compositions according to the invention in one embodiment thus preferably contain higher concentrations of invention compounds (i.e., total concentration of all invention compounds therein) than those which occur in nature and commercial forms of citrus. These concentrations are referred to as "concentrated amounts". Examples of preferred concentrations include greater than 0.25 mg/ml, 0.3, 0.8, 1, 2, 5, 8, 32, 128, 200 mg/ml, etc. With regard to invention compounds, the compounds in one embodiment of the invention are in a form distinct from that found in nature or commercially due to purity. The term "substantially pure" and "substantially pure form" refers to a purity greater than that found commercially and in nature for the invention compounds. These concentrations and forms are easily derminable by those of ordinary skill now that the present inventor has identified the active compounds responsible for the "grapefruit effect". Other language, phrases, etc. useful to describe the embodiments of the present invention and distinguish them patentably and otherwise from naturally or commercially occurring forms are found in the following patents assigned to the U.S. government and to others, all incorporated herein by reference: U.S. Pat. Nos. 4,708,948, 5,409,938, 5,455,251, 4,977,244, 5,462,956, 5,314,899, 5,104,977, 5,484,889, 5,591,770, 5,599,839, 5,672,607, 5,674,900, 5,648,354, 5,691,386, 5,681,829 and 5,654,432. Another description of how the present invention may be used, in what amounts, and how administered appears in U.S. Pat. No. 5,665,386, WO 97/15269 and WO 96/40192, all incorporated herein by reference.

The following patent applications, provisional or otherwise, are incorporated herein by reference: 60/056,382, 60/048,183, 60/043,878, 08/764,081 and 08/673,800.

Other compounds useful herein are described by the following formulae where R, L, E and HAr are as described above. As with the above compounds, these compounds include all stereoisomers, E–Z isomers, etc. Where naturally or commercially occurring, these compounds are preferably in the forms described above regarding purity, concentration, etc. These compounds may be optionally substituted as compounds of Formulae I–XVI are.

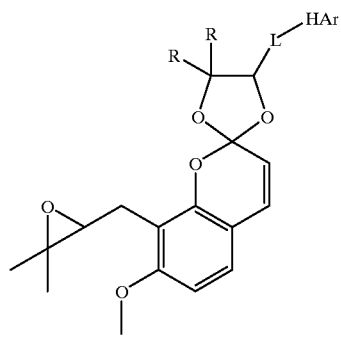

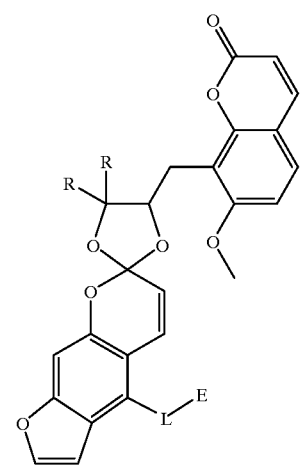

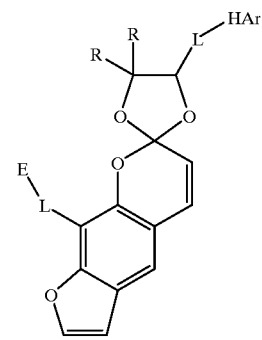

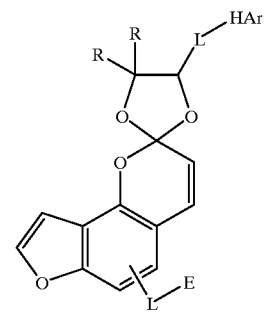

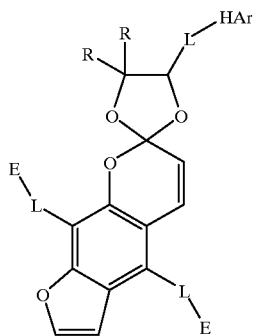
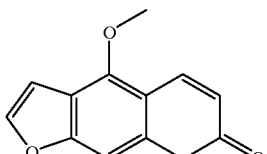
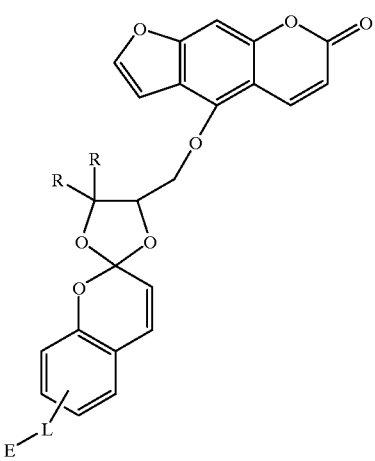
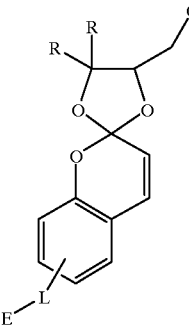
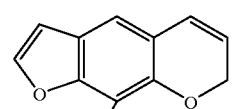
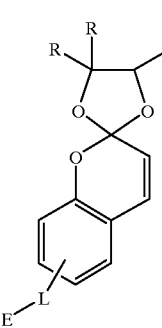
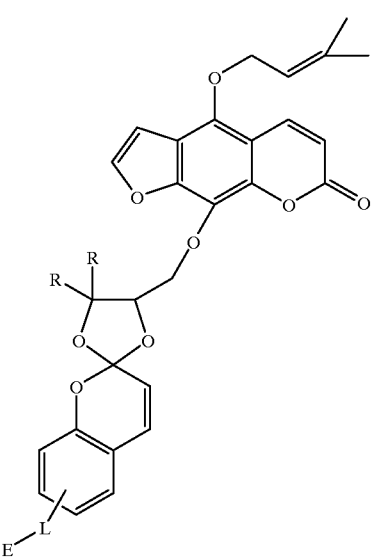
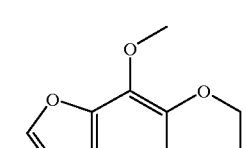
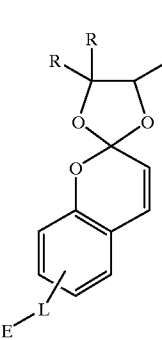

In the invention compounds a preferred group of sustituents, optional and otherwise, comprise the following: hydrogen, $C_1$–$C_4$ alkyl, —S($C_1$–$C_4$ alkyl), —O($C_1$–$C_4$ alkyl), —NH$_2$, —NH($C_1$–$C_4$ alkyl) —N($C_1$–$C_2$ alkyl) ($C_1$–$C_4$ alkyl), hydroxy, —O($C_1$–$C_2$ alkyl), fluoro, $C_1$–$C_6$ alkyl, chloro, bromo, iodo, $C_1$–$C_4$ alkoxy, —CF$_3$, —C(=O)O—($C_1$–$C_4$) alkyl, —OC(=O)($C_1$–$C_4$ alkyl), —OC(=O)N($C_1$–$C_4$ alkyl) ($C_1$–$C_2$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl) ($C_1$–$C_2$ alkyl), —S($C_1$–$C_4$ alkyl), —CN, —NO$_2$, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl) ($C_1$–$C_2$ alkyl).

Another group of preferred substituents, optional and otherwise, comprise: $C_1$–$C_{12}$ alkyl, aryl, ($C_1$–$C_4$ alkylene) aryl, phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl, $C_3$–$C_8$ cycloalkyl or ($C_1$–$C_6$ alkylene) ($C_3$–$C_8$ cycloalkyl), $C_1$–$C_4$ alkyl, benzyl, $C_1$–$C_4$ alkanoyl, $C_1$–$C_6$ alkoxy, —OC(=O) ($C_1$–$C_6$ alkyl), —OC(=O)N($C_1$–$C_4$ alkyl)($C_1$–$C_2$ alkyl), —S($C_1$–$C_6$ alkyl), amino, —NH($C_1$–$C_2$ alkyl), —N($C_1$–$C_2$ alkyl) ($C_1$–$C_4$ alkyl), —N($C_1$–$C_4$ alkyl)—CO—($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl) ($C_1$–$C_2$ alkyl), —SH, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl) ($C_1$–$C_2$ alkyl)

A third group of preferred substituents, optional and otherwise, comprise: —S($C_1$–$C_4$ alkyl) or —SO$_2$($C_1$–$C_4$ alkyl) ($C_1$–$C_6$ alkyl), —N($C_1$–$C_4$ alkyl) ($C_1$–$C_2$ alkyl), —S($C_1$–$C_4$ alkyl), —SO($C_1$–$C_4$ alkyl), —CO($C_1$–$C_4$ alkyl), —C(=O)H, —C(=O)O($C_1$–$C_4$ alkyl), $C_1$–$C_3$ alkoxy, dimethylamino, methylamino, ethylamino, —NHC(=O)CH$_3$, $C_1$–$C_3$ thioalkyl, —COOH, —C(=O)O($C_1$–$C_4$ alkyl), —C(=O)O($C_1$–$C_4$ alkyl), —NO$_2$, phenyl, naphthyl, thienyl, benzothienyl, pyridyl, quinolyl, pyrazinyl, furanyl, benzofuranyl, benzothiazolyl, benzisothiazolyl, benzisoxazolyl, benzimidazolyl, indolyl, benzoxazolyl or $C_3$–$C_8$ cycloalkyl, chloro, $C_1$–$C_6$ alkyl, —O($C_1$–$C_6$ alkyl) bromo, iodo, formyl, —CN, —CF$_3$, —NO$_2$, —NH$_2$, —NH($C_1$–$C_4$ alkyl), —N($C_1$–$C_2$ alkyl) ($C_1$–$C_6$ alkyl), —C(=O)O($C_1$–$C_4$ alkyl), —C(=O) ($C_1$–$C_4$ alkyl), —COOH, —SO$_2$NH($C_1$–$C_4$ alkyl), —SO$_2$N($C_1$–$C_2$ alkyl) ($C_1$–$C_4$ alkyl), —SO$_2$NH$_2$, —NHSO$_2$($C_1$–$C_4$ alkyl), —S($C_1$–$C_6$ alkyl) and —SO$_2$($C_1$–$C_6$ alkyl), fluoro, hydroxy, amino, methylamino, dimethylamino, acetyl, hydrogen, $C_1$–$C_4$ alkyl, halo (e,g., chloro, fluoro, iodo or bromo), hydroxy, —O($C_1$–$C_4$ alkyl), —C(=O) ($C_1$–$C_4$ alkyl), —C(=O)O ($C_1$–$C_4$ alkyl), —OCF$_3$, —CF$_3$, —CH$_2$OH or —CH$_2$O ($C_1$–$C_2$ alkyl) hydroxy, methoxy and fluoro.

Within these three groups of preferred substituents are also specific examples of HAr (i.e., $C_6$–$C_{24}$ aromatic groups or heteroaromatic groups).

In the present invention prodrugs and active metabolites of the invention compounds, compositions, etc. are included. Such prodrugs are compounds which give rise to an invention compound upon administration to a mammal such as a human. Active metabolites are compounds formed upon administration of an invention compound, composition, etc. to a mammal, preferably a human, which are first-pass effective. Some examples of invention prodrugs and metabolites include:

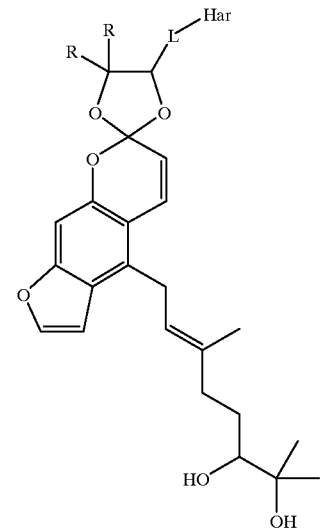

33
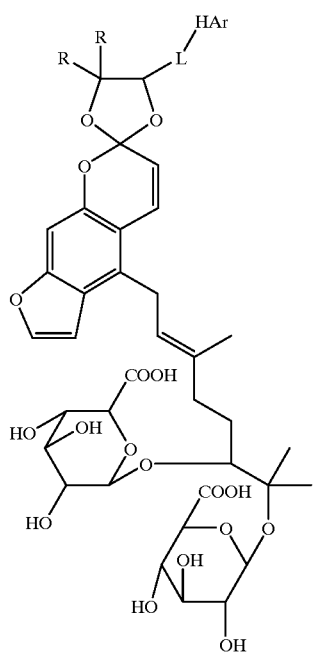
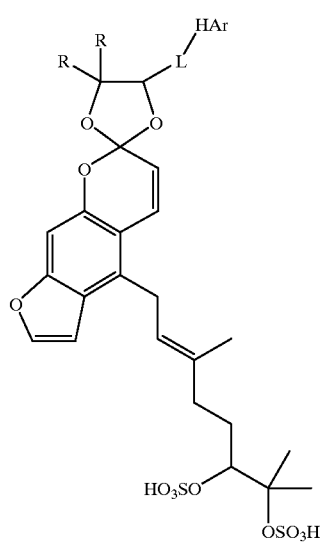
34
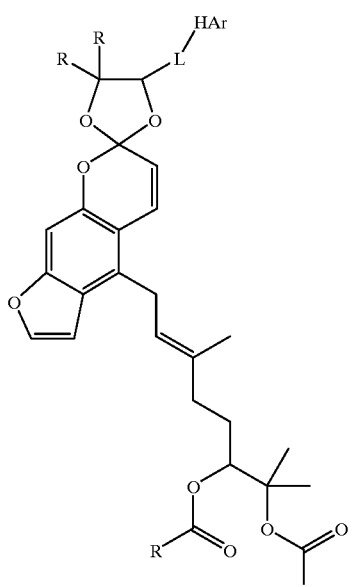
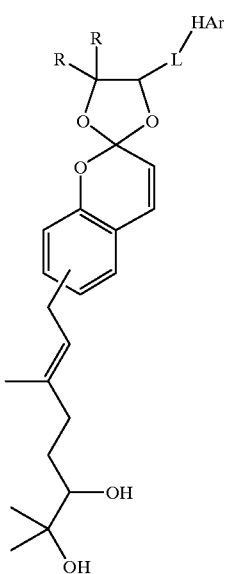

-continued

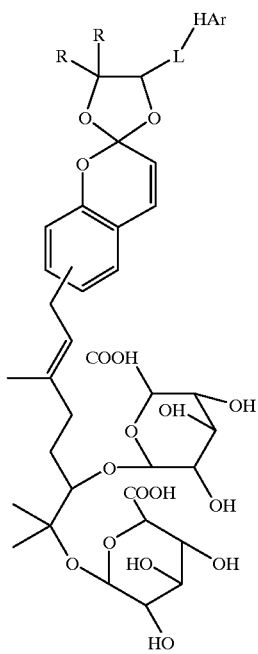

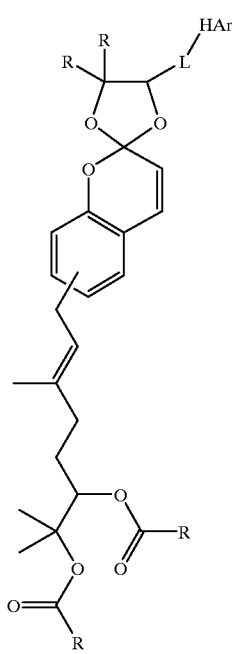

Invention compounds, metabolites, prodrugs, etc. may preferably be substituted with deuterium and/or fluorine to increase residence time in the patient/animal/etc.

Pharmaceutical carriers, diluents, excipients, etc. are known to those of skill in this art. Examples are provided in several above-noted patents and publications.

What is claimed is:

1. A method for preparing an edible product providing reliable first-pass effect inhibiting activity, comprising adding a compound of Formulae I–IV to a natural or commercial edible product:

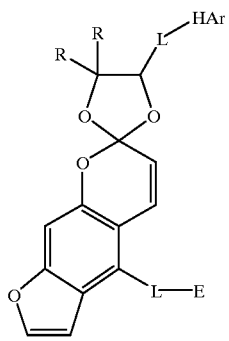

-continued

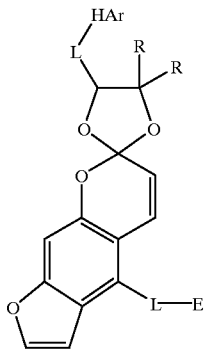

II

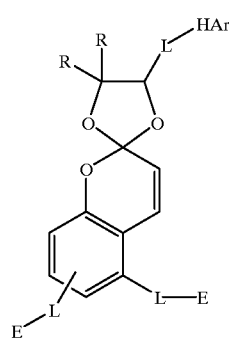

III

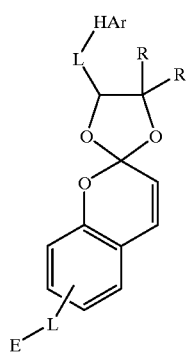

IV wherein in each of the above structures, R is, independently, H or an optionally substituted $C_1$–$C_{15}$ alkyl group, L is an optionally substituted $C_1$–$C_{15}$ linear or branched, saturated, monounsaturated or polyunsaturated alkyl group optionally terminated at one or both ends by oxygen, HAr is an optionally substituted $C_6$–$C_{24}$ aromatic group or heteroaromatic group optionally containing one or plural ring atoms selected from the group consisting of N, O, S, and P, and E is —OH, —COOH, —COOR where R is defined above or an optionally substituted $C_1$–$C_8$ linear or branched, saturated, monounsaturated or polyunsaturated alkyl group optionally interrupted by one or plural nonadjacent oxygen or sulphur atoms, or E is a $C_3$–$C_8$ optionally substituted cyclic saturated, monounsaturated or polyunsaturated alkyl group optionally interrupted by one or plural nonadjacent oxygen or sulphur atoms, or E is optionally substituted HAr, wherein the optional substituents for the groups R, L, HAr and E are selected from the group consisting of a $C_1$–$C_6$ linear, branched or cyclic alkyl group, —OH, halogen, a $C_1$–$C_5$ alkoxy group, a $C_1$–$C_5$ carbonyloxy group and a $C_1$–$C_5$ alkoxycarbonyl group.

2. A method as claimed in claim 1, wherein said natural or commercial edible product is a citrus juice.

3. A method as claimed in claim 2, wherein said citrus juice contains a compound of Formulae I–IV.

4. A method as claimed in claim 3, wherein said citrus juice is grapefruit juice.

5. A method as claimed in claim 1, wherein said natural or commercial edible product is a citrus-derived substance.

6. A method as claimed in claim 1, wherein said natural or commercial edible product comprises a taste-masking flavor.

7. A method as claimed in claim 1, wherein said natural or commercial edible product comprises a citrus-derived substance.

8. A method as claimed in claim 7, wherein said citrus-derived substance contains a compound of Formulae I–IV.

9. A method for preparing an edible product providing reliable first-pass effect inhibiting activity, comprising adding a compound of Formulae V–X to a natural or commercial edible product:

V

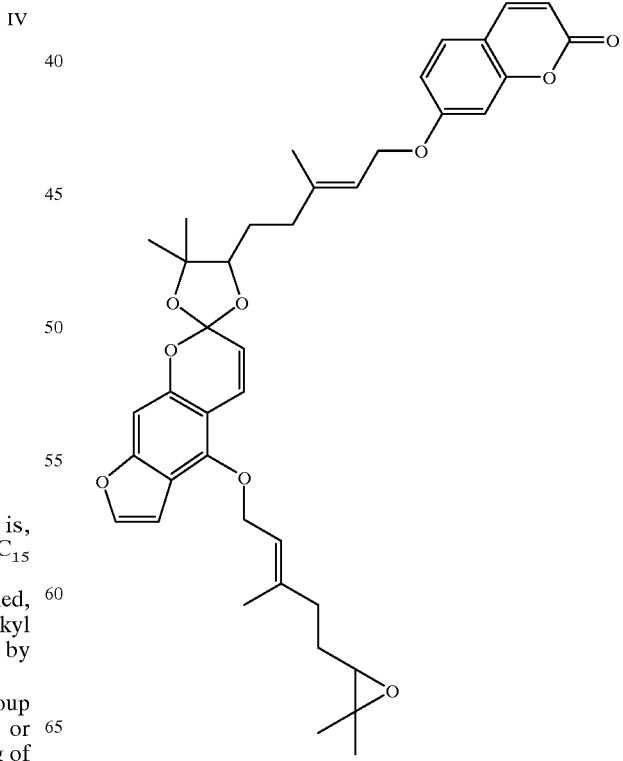

VI
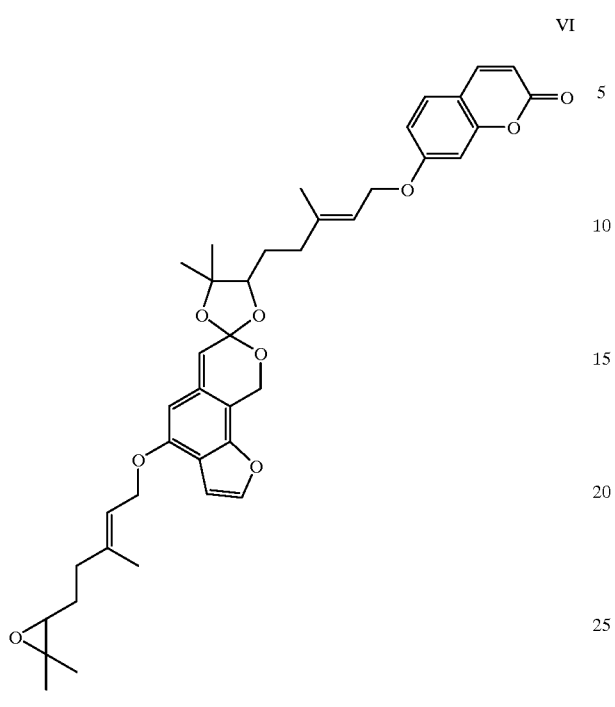
VII
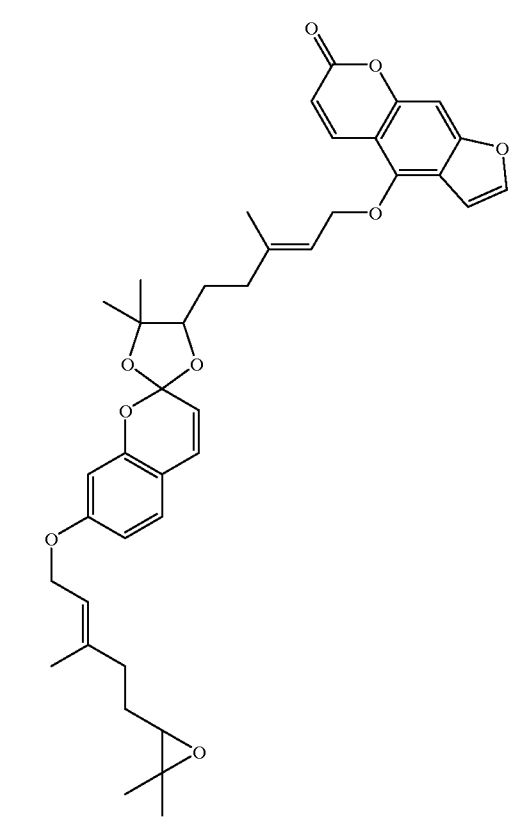
VIII
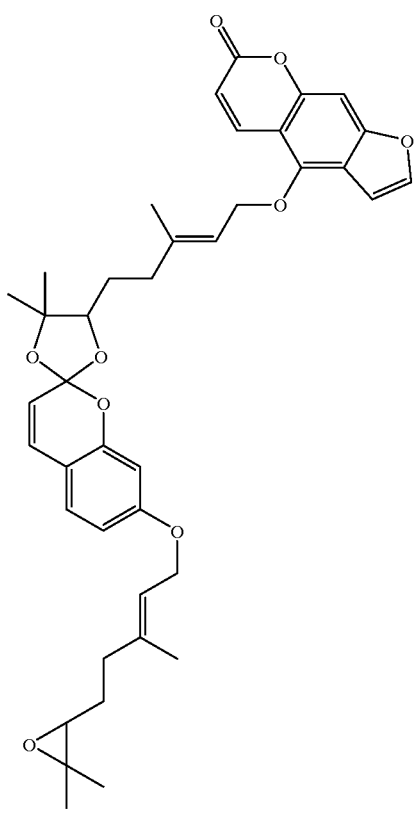
IX
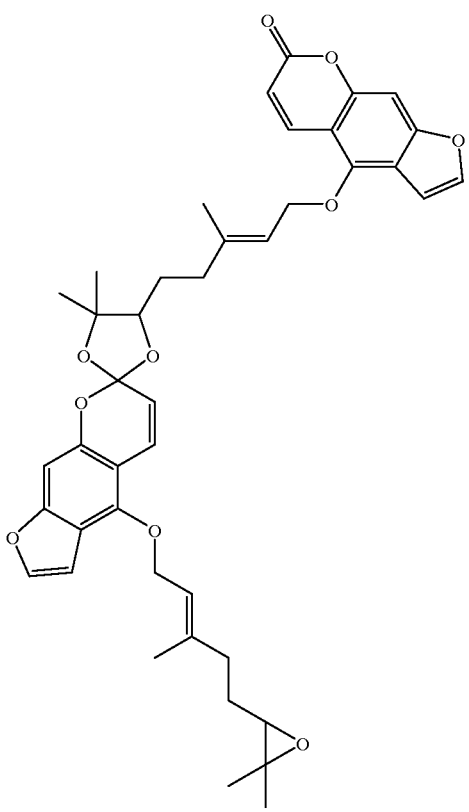

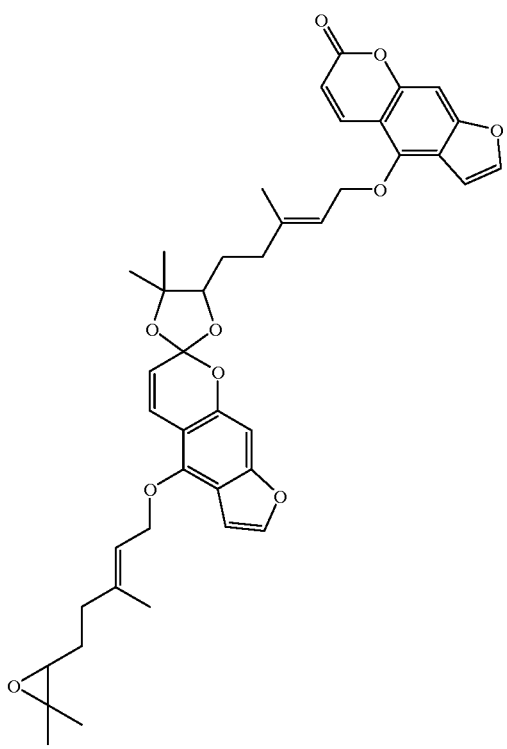

X

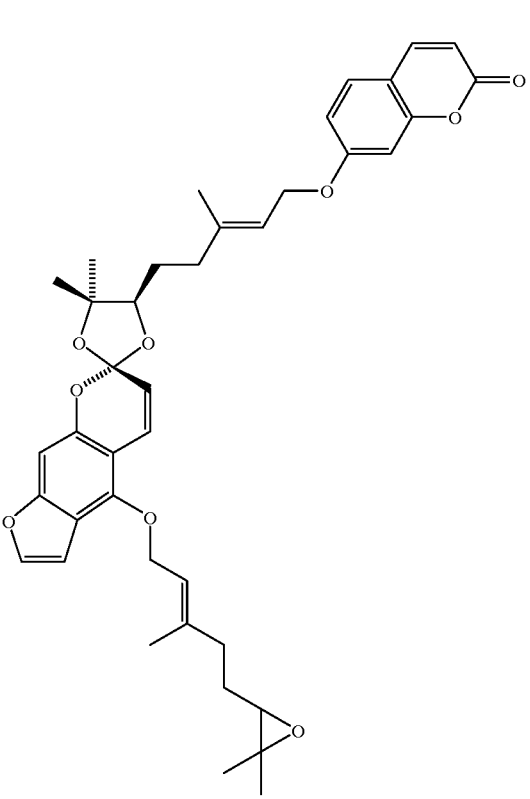

XI

10. A method as claimed in claim 9, wherein said natural or commercial edible product is a citrus-derived substance.

11. A method as claimed in claim 9, wherein said natural or commercial edible product comprises a taste-masking flavor.

12. A method as claimed in claim 1, wherein said natural or commercial edible product comprises a citrus-derived substance.

13. A method as claimed in claim 9, wherein said citrus-derived substance contains a compound of Formulae V–X.

14. A method as claimed in claim 9, wherein said natural or commercial edible product is a citrus juice.

15. A method for preparing an edible product providing reliable first-pass effect inhibiting activity, comprising adding a compound of Formulae XI–XVI to a natural or commercial edible product:

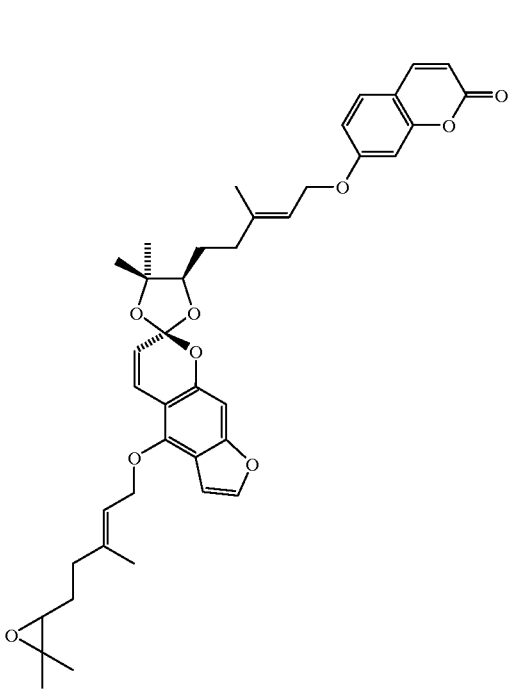

XII

XIII
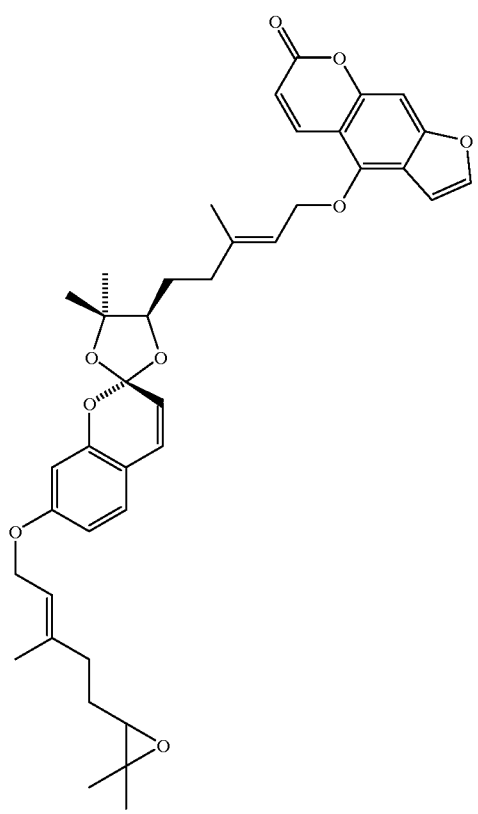
XIV
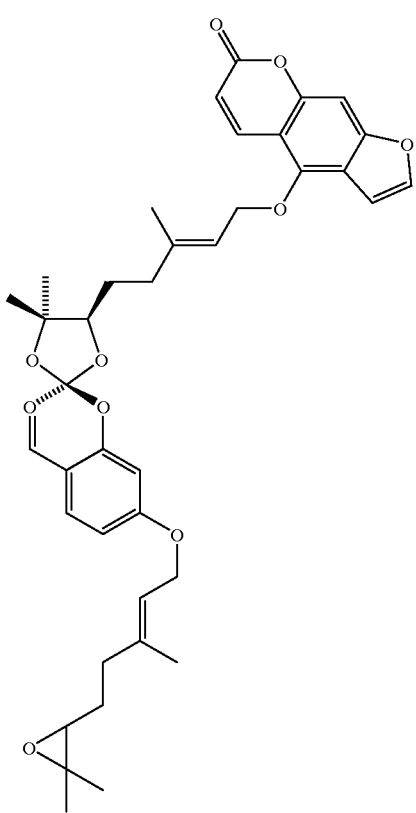
XV
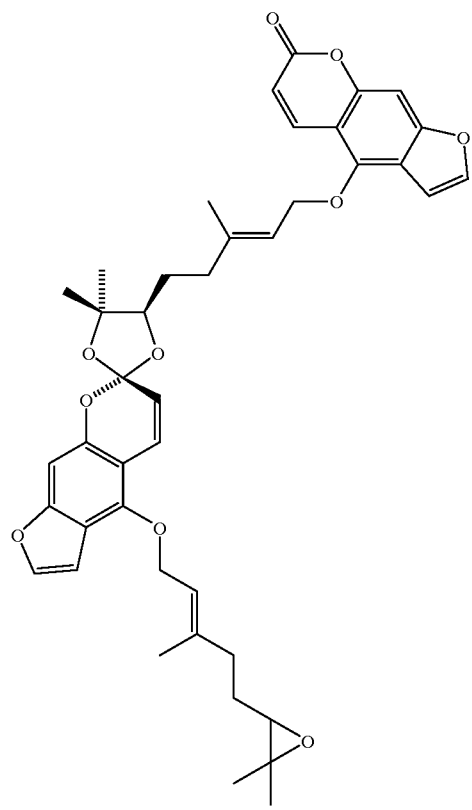
XVI
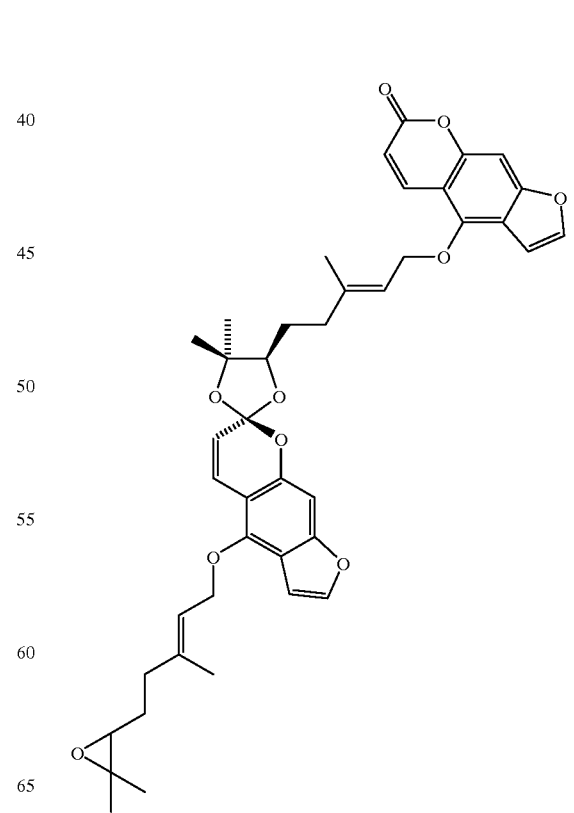

16. A method as claimed in claim 15, wherein said natural or commercial edible product is a citrus-derived substance.

17. A method as claimed in claim 15, wherein said natural or commercial edible product comprises a taste-masking flavor.

18. A method as claimed in claim 15, wherein said natural or commercial edible product comprises a citrus-derived substance.

19. A method as claimed in claim 15, wherein said citrus-derived substance contains a compound of Formulae XI–XVI.

20. A method as claimed in claim 15, wherein said natural or commercial edible product is a citrus juice.

\* \* \* \* \*

UNITED STATES PATENT AND TRADEMARK OFFICE
CERTIFICATE OF CORRECTION

PATENT NO. : 6,309,687 B1
DATED : October 30, 2001
INVENTOR(S) : Harris

It is certified that error appears in the above-identified patent and that said Letters Patent is hereby corrected as shown below:

<u>Title page,</u>
Item [75], the Inventor's information should read: -- [76] Inventor: James W. Harris, Cocoa Beach, FL (US) --
Item [63], the Related U.S. Application information should read:
-- Related U.S. Application Data
[63] Continuation of application No. 09/455,911, filed on Dec. 7, 1999, now Pat. No. 6,162,479, which is a continuation of application No. 09/255,874, filed on Feb. 23 1999, now Pat. No. 6,054,477, which is a continuation of application No. 08/997,259, filed on Dec. 23, 1997, now Pat. No. 6,063,809 --

Signed and Sealed this

Twenty-eighth Day of May, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO.     : 6,309,687 B1
DATED          : October 30, 2001
INVENTOR(S)    : Harris It is certified that error appears in the above-identified patent and that said Letters Patent is hereby corrected as shown below:

<u>Title page,</u>
Item [73], Assignee, should read:

-- [73]  Assignee:  Bioavailability Systems, LLC,
                   Cocoa Beach, FL (US) --

Signed and Sealed this

Nineteenth Day of August, 2003

JAMES E. ROGAN
*Director of the United States Patent and Trademark Office*